US006245774B1

(12) United States Patent
Warrellow et al.

(10) Patent No.: US 6,245,774 B1
(45) Date of Patent: *Jun. 12, 2001

(54) TRI-SUBSTITUTED PHENYL OR PYRIDINE DERIVATIVES

(75) Inventors: Graham John Warrellow, Northwood; Ewan Campbell Boyd, Tullibody; Rikki Peter Alexander, High Wycombe, all of (GB)

(73) Assignee: Celltech Therapeutics Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 08/492,855

(22) Filed: Jun. 20, 1995

(30) Foreign Application Priority Data

| Jun. 21, 1994 | (GB) | 9412384 |
| Jun. 21, 1994 | (GB) | 9412386 |
| Jun. 22, 1994 | (GB) | 9412493 |
| Aug. 5, 1994 | (GB) | 9415836 |

(51) Int. Cl.⁷ ............... C07D 213/38; C07D 213/643; C07D 213/74
(52) U.S. Cl. .............. 514/277; 514/357; 514/646; 514/656; 514/657; 514/764; 514/765; 546/87; 546/139; 546/152; 546/266; 546/268.4; 546/269.1; 546/270.1; 546/271.1; 546/271.4; 546/271.7; 546/272.4; 546/272.1; 546/272.7; 546/277.1; 546/277.4; 546/280.4; 546/281.4; 546/283.4; 546/284.1; 546/339
(58) Field of Search ............... 546/284, 87, 139, 546/152, 266, 339, 268.4, 269.1, 296.7, 270.1, 271.1, 271.4, 271.7, 272.1, 272.4, 272.7, 277.1, 277.4, 280.4, 281.1, 283.4, 284.1; 514/332, 252, 255, 256, 277, 292, 298, 306, 307, 311, 336, 338, 399; 548/203, 206, 217, 235, 247, 341.1, 576

(56) References Cited

U.S. PATENT DOCUMENTS

| 3,947,467 | 3/1976 | Verge et al. ............... 260/310 R |
| 4,012,495 | 3/1977 | Schmiechen et al. ........... 424/274 |
| 4,015,017 | 3/1977 | Gazave ........................... 424/331 |
| 4,153,713 | 5/1979 | Huth et al. ..................... 424/274 |
| 4,193,930 | 3/1980 | Schmiechen et al. .......... 260/326.5 |
| 4,303,649 | 12/1981 | Jones .............................. 424/177 |
| 4,548,940 | 10/1985 | Ife ................................... 514/272 |
| 4,694,009 | 9/1987 | Hubele et al. .................. 514/269 |
| 4,788,195 | 11/1988 | Torley et al. ................... 514/252 |
| 4,792,561 | 12/1988 | Walker et al. .................. 514/312 |
| 4,876,252 | 10/1989 | Torley et al. ................. 514/224.8 |
| 4,897,396 | 1/1990 | Hubele ............................ 514/275 |
| 4,921,862 | 5/1990 | Walker et al. .................. 514/312 |
| 4,966,622 | 10/1990 | Rempfler et al. .................. 71/92 |
| 4,971,959 | 11/1990 | Hawkins .......................... 514/150 |
| 4,987,132 | 1/1991 | Mase et al. ...................... 514/252 |
| 5,124,455 | 6/1992 | Lombardo ....................... 546/181 |
| 5,128,358 | 7/1992 | Saccomano et al. ........... 514/392 |
| 5,159,078 | 10/1992 | Rempfler et al. ............... 544/330 |
| 5,164,372 | 11/1992 | Matsuo et al. ................... 514/19 |
| 5,175,167 | 12/1992 | Zipperer et al. ................ 514/277 |
| 5,177,085 | 1/1993 | Naef ................................. 514/307 |
| 5,236,918 | 8/1993 | Amschler et al. ............... 514/247 |
| 5,274,002 | 12/1993 | Hawkins .......................... 514/530 |
| 5,298,511 | 3/1994 | Waterson ........................ 514/311 |
| 5,326,898 | 7/1994 | Chandraratna .................... 560/17 |
| 5,340,827 | 8/1994 | Beeley et al. ................... 514/352 |
| 5,491,147 | * 2/1996 | Boyd et al. ..................... 514/247 |
| 5,521,184 | 5/1996 | Zimmerman .................... 514/252 |
| 5,550,137 | 8/1996 | Beeley et al. ................... 514/354 |
| 5,580,888 | * 12/1996 | Warrellow et al. ............. 514/332 |
| 5,593,997 | 1/1997 | Dow et al. ...................... 514/258 |
| 5,608,070 | 3/1997 | Alexander et al. ............. 546/270 |
| 5,622,977 | * 4/1997 | Warrellow et al. ............. 514/336 |
| 5,633,257 | 5/1997 | Warrellow et al. ............. 514/277 |
| 5,674,880 | 10/1997 | Boyd et al. ..................... 514/307 |
| 5,691,376 | 11/1997 | Caggiano et al. .............. 514/532 |
| 5,693,659 | 12/1997 | Head et al. ...................... 514/357 |
| 5,698,711 | * 12/1997 | Palfreyman ....................... 549/66 |
| 5,716,967 | * 2/1998 | Kleinman ........................ 514/313 |
| 5,723,460 | * 3/1998 | Warrellow et al. ............. 514/247 |
| 5,728,708 | 3/1998 | Zimmermann ................. 514/275 |
| 5,739,144 | * 4/1998 | Warrellow et al. ............. 514/277 |
| 5,753,663 | 5/1998 | Flippin et al. .................. 514/257 |
| 5,776,958 | 7/1998 | Warrellow et al. ............. 514/345 |
| 5,780,477 | 7/1998 | Head et al. ...................... 514/277 |
| 5,780,478 | 7/1998 | Alexander et al. ............. 514/277 |
| 5,786,354 | 7/1998 | Warrellow et al. ............. 514/277 |
| 5,798,373 | 8/1998 | Warrellow ....................... 514/357 |
| 5,849,770 | 12/1998 | Head et al. ...................... 514/357 |
| 5,851,784 | 12/1998 | Owens et al. ..................... 435/19 |
| 5,859,034 | 1/1999 | Warrellow et al. ............. 514/357 |
| 5,866,593 | 2/1999 | Warrellow et al. ............. 514/336 |
| 5,891,896 | 4/1999 | Warrellow et al. ............. 514/357 |
| 5,922,741 | 7/1999 | Davis et al. ..................... 514/341 |

FOREIGN PATENT DOCUMENTS

| 250 1443 | 7/1975 | (DE) . |
| 0 233 461 A2 | 8/1987 | (EP) . |
| 0 295 210 A1 | 12/1988 | (EP) . |
| 0 337 943 A2 | 10/1989 | (EP) . |
| 0 393 500 | 10/1990 | (EP) . |
| 0 490 823 | 6/1991 | (EP) . |
| 0 470 805 | 2/1992 | (EP) . |
| 0497564A1 | 8/1992 | (EP) . |
| 0 511 865 | 11/1992 | (EP) . |
| 0 537 742 | 4/1993 | (EP) . |
| 0 564 409 A1 | 10/1993 | (EP) . |
| 2313422 | * 12/1976 | (FR) . |
| 2 545 356 A1 | 11/1984 | (FR) . |
| 1588639 | 4/1981 | (GB) . |
| 3-77872 | 4/1991 | (JP) . |
| 3-77923 | 4/1991 | (JP) . |
| WO 87/06576 | 11/1987 | (WO) . |
| WO 91/15451 | 10/1991 | (WO) . |
| WO 91/16892 | 11/1991 | (WO) . |
| WO 92/00968 | 1/1992 | (WO) . |
| WO 92/06085 | 4/1992 | (WO) . |
| WO 92/06963 | 4/1992 | (WO) . |
| WO 92/07567 | 5/1992 | (WO) . |
| WO 92/12961 | 8/1992 | (WO) . |
| WO 92/19594 | 11/1992 | (WO) . |
| WO 92/19602 | 11/1992 | (WO) . |
| WO 93/10118 | 5/1993 | (WO) . |
| WO 93/19748 | 10/1993 | (WO) . |
| WO 94/02465 | 2/1994 | (WO) . |
| WO 94/10118 | 5/1994 | (WO) . |
| WO 94/13661 | 6/1994 | (WO) . |
| WO 94/12461 | * 6/1994 | (WO) . |

| | | |
|---|---|---|
| WO 94/14742 | 7/1994 | (WO). |
| WO 94/20446 | 9/1994 | (WO). |
| WO 94/20455 | 9/1994 | (WO). |
| WO 95/04046 * | 2/1995 | (WO). |
| WO 95/09847 | 4/1995 | (WO). |
| WO 95/09851 | 4/1995 | (WO). |
| WO 95/09852 | 4/1995 | (WO). |
| WO 95/09853 | 4/1995 | (WO). |
| WO 95/17386 | 6/1995 | (WO). |
| WO 95/31451 | 11/1995 | (WO). |
| WO 95/33727 | 12/1995 | (WO). |
| WO 95/35281 | 12/1995 | (WO). |
| WO 95/35283 | 12/1995 | (WO). |
| WO 96/14843 | 5/1996 | (WO). |
| WO 97/09297 | 3/1997 | (WO). |
| WO 97/09325 | 3/1997 | (WO). |
| WO 98/28281 | 7/1998 | (WO). |
| WO 98/58926 | 12/1998 | (WO). |

OTHER PUBLICATIONS

Yamato et al., Chem. Pharm. Bull., vol. 23, No. 12, pp. 3101–3105, 1975.*

Barton et al., Tetrahedron, vol. 46, No. 21, pp. 7587–7598, 1990.*

Hanna et al., Bull. Fac. Pharm., vol. 32, No. 3, pp. 353–359, 1994.*

Tollari et al., J. Chem. Soc., No. 15, pp. 1741–1742, 1994.*

Fitzgerald et al., Tetrahedron Letters, vol. 35, No. 49, 1994.*

Chemical abstracts, registry No. 2732–15–2, pre–1967.*

Chemical abstracts, registry No. 4593–13–9, pre–1967.*

Caplus accession No. 1971:434722, Bortolus et al., "cis–trans Isomerization of azastilbenes photosensitized by biacetyl," Mol. Photochem., vol. 2, No. 4, pp. 311–321, 1970.*

Caplus accession No. 1973:71853, Kaiser et al., "Selective metalations of methylated pyridines and quinolines," J. Org. Chem., vol. 38, No. 1, pp. 71–75, 1973.*

Ashton, "Selective Type IV Phosphodiesterase Inhibitors as Antiasthmatic Agents. The Syntheses and Biological Activities of 3–(Cyclopentyloxy)–4–methyoxybenzamides and Analogues" J. Med. Chem. 37: 1696–1703 (1994).

Beavo & Reifsnyder, "Primary Sequence of Cyclic Nucleotide Phosphodiesterase Isozymes and the Design of Selective Inhibitors" TIPS 11: 150–155 (1990).

Buu–Hoi, N.P. et al., "Bromination of Some 1,2,2–Triarylethylenes" J. of Organic Chemistry, 1261–1263 (Sep., 1958).

Buu–Hoi et al., "New Method for the Synthesis of ω,ω–Diarylacetophenones Aminated in the Aromatic Nucleus. Plynitration of Triarylethylenes" Chemical Abstracts 61: 16006h (1964).

Chemical Abstracts. Registry Handbook—Number Section. Printed Issues Columbus US *compounds with registry numbers 95992–21–5; 95971–60–1; 90053–37–5; 82668–18–6; 80395–25–1; 49610–49–3.

El–Wakil et al., "Study of the proton magnetic resonance of methoxytamoxifen towards ortho–substitiution" Chemical Abstracts 116: 255248t (1992).

Hirose et al., "Styrene Derivatives and Electrophotpgraphic Photoreceptor Containing Them" Chemical Abstracts 118: 136183z (1993).

Lisle, H. et al., "IL–2–Induced Eosinophilia in the Rat Pleural Cavity: The Effect of Dexamethasone and Indomethacin", Br. J. Pharmacol. 1993, 108, 230.

Livi et al., "Cloning and Expression of cDNA for a Human Low–$K_m$3 Rolipram–sensitive Cyclic AMP Phosphodiesterase", Molecular and Cellular Biol. 1990, 10, 2678.

Ishikura, M. et al., "An Efficient Synthesis of 3–Heteroarylpyridines via Diethyl–(3–pyridyl)–borane" Synthesis pp. 936–938 (1984).

Manhas et al., "heterocyclic Compounds XII. Quinazoline Derivatives as Potential Antifertility Agents(1)" J. Heterocyclic Chem: 711–715 (1979).

Meyers, A.J. et al., "Oxazolines. XI. Synthesis of Functionalized Aromatic and Aliphatic Acids. A Useful Protecting Group for Carboxylic Acids Against Grignard and Hydride Reagents", J. Org. Chem. 1974, 39, 2787.

Mezheritskaya, "Synthesis and properties of carboxonium het=erocyclic systems. VII. Synthesis and properties of 2–benzyl–substituted 1,3–dioxolanium salts" Chem. Abs. 93: 95160j p. 635(1980).

Mitsunobu, O., "The Use of Diethyl Azodicarboxylate and Triphenylphosphine in Synthesis and Transformation of Natural Products" Synthesis 1–28 (1981).

Nicholson et al., "Differential Modulation of Tissue Function and Therapeutic Potential of Selective Inhibitors of Cyclic Nucleotide Phosphodiesterase Isoenzymes" TIPS 12: 19–27 (1991).

O'Connor et al., "Voltammetry and Controlled Potential Oxidation of 3,4–dimethoxypropenylbenzene at a rotating platinum electrode in unbuffered acetonitrile and in acetonitrile–pyridine solution" Chemical Abstracts 60(8) #10203.4 (Apr. 13, 1964).

Porter et al., "Preparation of 6–phenyl–3–(5–tetrazolyl)pyridin–=2(H)–one Derivatives as Cyclic AMP–dependent Protein Kinase Agonists" Chem. Abstract 117(9): 90296n (1992).

Ramalingam, Deshmukh and Sattur, "Synthesis and Pharmacology of 2,5–Disubstituted 1,3,4–Zxadiazoles" J. Indian Chem. Soc. vol. 58(3) 269–271 (1981).

Reddy et al., "Inhibition of Breast Cancer Cell Growth in Vitro by a Tyrosine Kinase Inhibitor" Cancer Research 52: 3636–3641 (1992).

Schneider et al., "Catechol Estrogens of the 1,1, 2–Triphenylbut–1–ene Type: Relationship Between Structure, Estradiol Receptor Affinity, Estrogenic and Antiestrogenic Properties, and Mammary Tumor Inhibiting Activities" J. Med. Chem. 29: 1355–1362 (1986).

Seitz et al., "Fluorotamoxifen. A Caveat on the Generality of Electrophilic Destannylation" Chemical Abstracts 111: 57133k (1989).

Sharp, M.J. et al., "Synthetic Connections to the Aromatic Directed Metalation Reaction. Functionalized Aryl Boronic Acids by Ipso Borodesilyation; General Synthesis of Unsymmetrical iphenyls and n–Terphenyls" Tetrahedron Lett 28: 5093–5096 (1987).

Thompson, W.J. and Guadino, J., "A General Synthesis of 5–Arylnicotinates" J. Org. Chem. 49: 5237–5243 (1984).

Yeadon et al., "Mechanisms Contributing to Ozone–Induced Bronchial Hyperreactivity in Guinea Pigs", Pulmonary Pharm. 1992, 5, 39.

Yoneda et al., "The Antiproliferative Effects of Tyrosine Kinase Inhibitors Tyrphostins on a Human Squamous Cell Carcinoma in Vitro and in Nude Mice" Cancer Research 51: 4430–4435 (1991).

Green & Wuts, "Protective Groups in Organic Synthesis", John Wiley & Sons, 1981.

Miyaura, N. et al., "The Palladium–Catalyzed Cross–Coupling Reaction of Phenylboronic Acid with Haloarenes in the Presence of Bases", *Synth. Comm.* 1981, 11, 513–519.

Trost and Fleming, "Comprehensive Organic Synthesis", vol. 3, Pergamon Press, New York, pp. 531–541, 1991.

Chemical Abstracts, "Hypoglycemic Pharmaceuticals Containing Manzammide Derivatives", *Chem. Abstr.*, 1983, 99(6), No. 43558Z.

Dent et al., "Inhibition of eosinophil cyclic nucleotide PDE activity and opsonised zymosan–stimulated respiratory burst by 'type IV'–selective PDE inhibitors", *Br. J. Pharmacol.*, 1991, 103, 1339–1346.

Grammaticakis, "Contribution A L'Etude de L'Absortion Dans L'Ultraviolet Moyen Et Le Visible Des N–Aroyl–Arylamines. IV. 2,3–, 3,4– et 2,4–, dimethoxybenzoylarylamines", *Bulletin DeLa Societa Chemique De France*, 1965, 848–858.

Heaslip et al., "Phosphodiesterase–IV Inhibition, Respiratory Muscle Relaxation and Bronchodilation by WAY–PDA–641", *J. Pharm. Exper. Ther.*, 1993, 268(2), 888–896.

Karlsson et al., "T–Lymphocyte and Inflammatory Cell Research in Asthma", Joller, G. et al. (eds.), Academic Press, 1993, 323–347.

Mathison et al., "Synthesis and Hypotensive Properties of Tetrahydroixoquinolines", *J. Med. Chem.*, 1973, 16(4), 332–336.

Shioiri et al., "New Methods and Reagents in Organic Synthesis. 3. Diethyl Phosphorocyanidate: A New Reagent for C–Acylation", *J. Org. Chem.*, 1978, 43, 3631–3632.

Takeuchi, I. et al., "On the Antimocrobiol Activity and Syntheses of Carbanilide and Salicylanilide Derivatives", *Chem. Abstr.*, 1983, 98, No. 125577y.

Tominaga et al., "Polarized Ethylenes. IV. Synthesis of Polarized Ethylenes Using Thioamides and Methyl Dithiocarboxylates and Their Application to Syntheses of Pyrazoles, Pyrimidines, Pyrazolo[3,4–d]pyrimidines, and 5–Aza [2.2.3]cyclazines", *J. Het. Chem.*, 1990, 27, 647–660.

Vidal et al., "Electrophilic Amination: Preparation and Use of N–Boc–3–(4–cyanophenyl)oxaziridine, a New Reagent That Transfers a N–Boc Group to N– and C–Nucleophiles", *J. Org. Chem.*, 1993, 58, 4791–4793.

Chatterjee, A. et al., "Total Synthesis of Ring–C Aromatic 18–Nor Steroid", *Tetrahedron*, 1980, 36, 2513–2519.

Clayton, S.E. et al., "Direct Aromatic tert–Butylation during the Synthesis of Thiochroman–4–ones", *Tetrahedron*, 1993, 49(4), 939–946.

Collins, R.F. et al., "The Chemotherapy of Schistosomiasis. Part IV. Some Ethers of 4–Amino–2–methoxyphenol", *J. Chem. Soc.*, 1961, 1863–1879.

Degani, I. et al., "Cationi etero–aromatici Nota VI—Sintesi di alcuni derivati del perclorato di tiacromilio", *Boll Sci. Fac. Chim. Ind. Bologna*, 1966, 24(2–3), 75–91 (English Summary Only).

Geissler et al., "Biochemical and Biological Activity of a Novel Class of Tyrosine Protein Kinase Inhibitors", *J. Biol. Chem.*, 1990, 265(36), 22255–22261.

Griffin, R.W. et al., "1–Methyl–7–halo–2–naphthalenecarboxylic Acid Derivatives", *J. Organic Chem.*, 1964, 29(8), 2109–2116.

Gupta, A.S. et al., "Friedel–Crafts Condensation of Ethyl Allylmalonate with Anisole", *Tetrahedron*, 1967, 23, 2481–2490.

Hart et al., "Alkylation of Phenol with a Homoallylic Halide", *J. Am. Chem. Soc.*, 1963, 85, 3269–3273.

Johnson et al., "Identification of Retinoic Acid Receptor β Subtype Specific Agonists", *J. Med. Chem.*, 1996, 39(26), 5027–5030.

Lehmann, J. et al., "Lactones; XIII. Grignard Reaction Followed By Phase–Transfer Oxidation: A Convenient Synthesis of γ,γ–Distributed γ–Butyrolactones from γ–Butyrolactone", *Synthesis*, 1987, 1064–1067 (English abstract only).

Meyers, A.I. et al., "The Synthesis of 2–Pyridones from Cyclic Cyano Ketones. A New Aromatization Procedure for Dihydro–2–pyridones", *J. Org. Chem.*, 1964, 29, 1435–1438.

Chan, A.C. et al., "The Role of Protein Tyrosine Kinases and Protein Tyrosine Phosphatases in T Cell Antigen Receptor Signal Transduction", *Annu. Rev. Immunol.*, 1994, 12, 555–592.

Daves, G.D. et al., "Pyrimidines. XIII. 2– and 6–Substituted 4–Pyrimidinecarboxylic Acids", *J. Of Hev. Chem.*, 1964, 1, 130–133.

Dietl, F. et al., "Chinone von Benzo–und Dibenzokronenethern", *Synthesis*, 1985, 626–631.

Geissler, J.F. et al., "Thiazolidine–Diones. Biochemical and Biological Activity of a Novel Class of Tyrosine Protein Kinase Inhbitors", *J. Of Biol. Chem.*, 1990, 265(36), 22255–22261.

Hanks, S.K. et al., "The eukaryotic protein kinase superfamily: kinase (catalytic) domain structure and classification", *FASEB J.*, 1995, 9, 576–596.

Iwashita, S. et al., "Signal Transduction System for Growth Factor Receptors Associated with Tyrosine Kinase Activity: Epidermal Growth Factor Receptor Singalling and Its Regulation", *Cellular Signalling*, 1992, 4(2), 123–132.

Newton, A.C., "Protein Kinase C: Structure, Function, Regulation", *J. Biol. Chem.*, 1995, 270(48), 28495–28498.

Ohtani, Y. et al., "Studies on Pitch Problems Caused by Pulping and Bleaching of Tropical Woods. XIV. Chemistry of the Aurone Derivatives at the Conventional Bleaching Stages", *Acta Chem. Scand.*, 1982, 613–621.

Pines, J., "Cyclins and cyclin–dependent kinases: take your partners", *TIBS*, 1993, 18, 195–197.

Plé, N. et al., "Metalation of Diazines. XI. Directed Ortho–Lithiation of Fluoropyrimidines and Application to Synthesis of an Azacarboline", *J. Heterocyclic Chem.*, 1994, 31, 1311–1315.

Sánchez, H.I. et al., "Formal Total Syntehsis of β–Pipitzol", *Tetrahedron*, 1985, 41(12), 2355–2359.

Sakakibara, K. et al., "Preparation of N–pyridyl–4–(benzyloxy)benzamides as Cardiotonics", *Chem. Abstr.* 1988, 108, No. 131583p.

Tsutsumi, K. et al., "Preparation of (Dialkoxyphosphinoylmethyl)benzamides as Antihyperlipidemics", *Chem. Abstr.* 1990, 113, No. 6599a.

Kefalas, P. et al., "Signalling by the p60$^{c-src}$ Family of Protein–Tyrosine Kinases", *Int. J. Biochem. Cell Biol.*, 1995, 27(6), 551–563.

Kroon, A.P. et al., "SN(ANRORC) [addition nucleophilic ring opening–ring closing]–mechanism. XIII. SN(ANRORC) mechanism in the amination of 2–substituted 4–phenylpyrimidines with potassijm amide in liquid ammonia," *Recl. Trav. Chim. Pays–Bas*, 1974, 93(12), 325–328, Chemical Abstract No. 83:43256.

Pickett, W.C. et al., "Modulation of Eicosanoid Biosynthesis by Novel Pyridinylpyrimidines", *Ann. N.Y. Acad. Sci.*, 1994, 744, 299–305.

Spada, A.P. et al., "Small Molecule Inhibitors of Tyrosine Kinase Activity", *Exp. Opin. Ther. Patents*, 1995, 5(8), 805–817.

Yamaguchi, H., "Guanidinobenzene derivatives as anticoagulants", *Chem. Absts.*, 1989, 110, 655 (Abstract No. 94706z).

Zimmermann, J. et al., "Phenylamino–Pyrimdine (PAP) Derivatives: A New Class of Potent and Selective Inhibitors of Protein Kinase C (PKC)", *Arch. Pharm.*, 1996, 329(7), 371–376.

Zimmermann, J. et al., "Phenylamino–Pyrimidine (PAP)— Derivatives: A New Class of Potent and Highly Selective PDGF–Receptor Autophosphorylation Inhibitors", *Bioorg. Med. Chem. Lett.*, 1996, 6(11), 1221–1226.

Zimmermann, J. et al., "Potent and Selective Inhibitors of the ABL–Kinase Phenylamino–Pyrimidine (PAP) Derivatives", *Bioorg. Med. Chem. Lett.*, 1997, 7(2), 187–192.

Ames, D.E. et al., "Some Dipyridylalkanes", *J. Chem. Soc.*, 1962, 1475–1481.

Nanjo et al., "Preparation of 2–anilinopyrimidines as agricultural fungicides", *Chem. Abstr.*, 1992, 116(21), No. 116:209703q.

\* cited by examiner

*Primary Examiner*—Robert E. L. Sellers
(74) *Attorney, Agent, or Firm*—Woodcock Washburn Kurtz Mackiewicz & Norris LLP

(57) ABSTRACT

Compounds of general formula (1) are described:

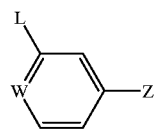

(1)

wherein

=W— is (1) =C(Y)— where Y is a halogen atom, or an alkyl or —XR$^a$ group where X is —O—, —S(O)$_m$— [where m is zero or an integer of value 1 or 2], or —N(R$^b$)— [where R$^b$ is a hydrogen atom or an optionally substituted alkyl group] and R$^a$ is a hydrogen atom or an optionally substituted alkyl group or, (2) =N—;

L is (1) a —C(R)=C(R$^1$)(R$^2$) or [—CH(R)]$_n$CH(R$^1$)(R$^2$) group; is (2) a —(X$^a$)$_n$Alk'Ar', or Alk'X$^a$Ar' group; or is (3) X$^a$R$^1$;

Z is a group (A), (B), (C) or (D):

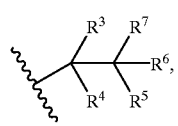

(A)

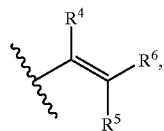

(B)

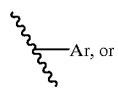

(C)

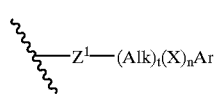

(D)

wherein

Ar is a monocyclic or bicyclic aryl group optionally containing one or more heteroatoms selected from oxygen, sulphur or nitrogen atoms;

Z$^1$ is a group —NR$^{12}$C(O)— [where R$^{12}$ is a hydrogen atom or an optionally substituted alkyl or (Alk)$_t$Ar group], —C(O)NR$^{12}$—, —NR$^{12}$C(S)—, —C(S)NR$^{12}$—, —C≡C—, —NR$^{12}$SO$_2$—, or —SO$_2$NR$^{12}$—;

Alk is an optionally substituted straight or branched alkyl chain optionally interrupted by an atom or group X;

t is zero or an integer of value 1, 2 or 3;

R$^3$ is a hydrogen or a fluorine atom or an optionally substituted straight or branched alkyl group or an OR$^{11}$ group [where R$^{11}$ is a hydrogen atom or an optionally substituted alkyl, alkenyl, alkoxyalkyl, alkanoyl, formyl, carboxamido or thiocarboxamido group];

R$^4$ is a hydrogen atom or an optionally substituted alkyl, —CO$_2$R$^8$, —CSNR$^9$R$^{10}$, —CN, —CH$_2$CN, or —(CH$_2$)$_t$Ar group where t is zero or an integer of value 1, 2 or 3 and Ar is a monocyclic or bicyclic aryl group optionally containing one or more heteroatoms selected from oxygen, sulphur or nitrogen atoms; provided that when L is a group of type (2) or (3) above then Z is a group of type (A) or type (B) in which R$^4$ is a —(CH$_2$)$_t$Ar group;

R$^5$ is a group —(CH$_2$)$_t$Ar;

R$^6$ is a hydrogen or a fluorine atom, or an optionally substituted alkyl or —CO$_2$R$^8$, —CONR$^9$R$^{10}$, —CSNR$^9$R$^{10}$, —CN or —CH$_2$CN group;

R$^7$ is a hydrogen or a fluorine atom, an optionally substituted straight or branched alkyl group, or an OR$^c$ group where R$^c$ is a hydrogen atom or an optionally substituted alkyl or alkenyl group, alkoxyalkyl, alkanoyl, formyl, carboxamido or thiocarboxamido group; and the salts, solvates, hydrates, prodrugs and N-oxides thereof.

Compounds according to the invention are phosphodiesterase type IV inhibitors and are useful in the prophylaxis and treatment of disease such as asthma where unwanted inflammatory response or muscular spasm is present.

17 Claims, No Drawings

TRI-SUBSTITUTED PHENYL OR PYRIDINE DERIVATIVES

This invention relates to a novel series of tri-substituted phenyl derivatives, to processes for their preparation, to pharmaceutical compositions containing them, and to their use in medicine.

Many hormones and neurotransmitters modulate tissue function by elevating intra-cellular levels of adenosine 3',5'-cyclic monophosphate (cAMP). The cellular levels of cAMP are regulated by mechanisms which control synthesis and breakdown. The synthesis of cAMP is controlled by adenyl cyclase which may be directly activated by agents such as forskolin or indirectly activated by the binding of specific agonists to cell surface receptors which are coupled to adenyl cyclase. The breakdown of cAMP is controlled by a family of phosphodiesterase (PDE) isoenzymes, which also control the breakdown of guanosine 3',5'-cyclic monophosphate (cAMP). To date, seven members of the family have been described (PDE I–VII) the distribution of which varies from tissue to tissue. This suggests that specific inhibitors of PDE isoenzymes could achieve differential elevation of cAMP in different tissues, [for reviews of PDE distribution, structure, function and regulation, see Beavo & Reifsnyder (1990) TIPS, 11: 150–155 and Nicholson et al (1991) TIPS, 12: 19–27].

There is clear evidence that elevation of cAMP in inflammatory leukocytes leads to inhibition of their activation. Furthermore, elevation of cAMP in airway smooth muscle has a spasmolytic effect. In these tissues, PDE IV plays a major role in the hydrolysis of cAMP. It can be expected, therefore, that selective inhibitors of PDE IV would have therapeutic effects in inflammatory diseases such as asthma, by achieving both anti-inflammatory and bronchodilator effects.

The design of PDE IV inhibitors has met with limited success to date, in that many of the potential PDE IV inhibitors which have been synthesised have lacked potency and/or have been capable of inhibiting more than one type of PDE isoenzyme in a non-selective manner. Lack of a selective action has been a particular problem given the widespread role of cAMP in vivo and what is needed are potent selective PDE IV inhibitors with an inhibitory action against PDE IV and little or no action against other PDE isoenzymes.

We have now found a novel series of tri-substituted phenyl derivatives, members of which are potent inhibitors of PDE IV at concentrations at which they have little or no inhibitory action on other PDE isoenzymes. These compounds inhibit the human recombinant PDE IV enzyme and also elevate cAMP in isolated leukocytes. The compounds of the invention are therefore of use in medicine, especially in the prophylaxis and treatment of asthma.

Thus according to one aspect of the invention, we provide a compound of formula (1)

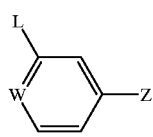

(1)

wherein

=W— is (1) =C(Y)— where Y is a halogen atom, or an alkyl or —$XR^a$ group where X is —O—, —$S(O)_m$— [where m is zero or an integer of value 1 or 2], or —$N(R^b)$— [where $R^b$ is a hydrogen atom or an optionally substituted alkyl group] and $R^a$ is a hydrogen atom or an optionally substituted alkyl group or, (2) =N—;

L is (1) a —C(R)=$C(R^1)(R^2)$ or [—CH(R)]$_n$CH$(R^1)(R^2)$ group where R is a hydrogen or a fluorine atom or a methyl group, and $R^1$ and $R^2$, which may be the same or different, is each a hydrogen or fluorine atom or an optionally substituted alkyl, alkenyl, alkynyl, alkoxy, alkylthio, —$CO_2R^8$ [where $R^8$ is a hydrogen atom or an optionally substituted alkyl, aralkyl or aryl group], —$CONR^9R^{10}$ [where $R^9$ and $R^{10}$, which may be the same or different are defined for $R^8$], —$CSNR^9R^{10}$, —CN or —$NO_2$ group, or $R^1$ and $R^2$, together with the C atom to which they are attached are linked to form an optionally substituted cycloalkyl, cycloalkenyl or heterocycloaliphatic group and n is zero or the integer 1; or is (2) —$(X^a)_n$Alk'Ar', or —Alk'$X^a$Ar' where $X^a$ is a group X, Ar' is an optionally substituted heterocycloaliphatic, or an optionally substituted monocyclic or bicyclic aryl group optionally containing one or more heteroatoms selected from oxygen, sulphur or nitrogen atoms, Alk' is an optionally substituted straight or branched alkylene, alkenylene or alkynylene chain optionally interrupted by one or more $L^1$ atoms or groups [where $L^1$ is a linker atom or group] and n is zero or the integer 1; or is (3) $X^a$R' where R' is Ar' or is an optionally substituted polycycloalkyl or polycycloalkenyl group optionally containing one or more —O—, or —S— atoms or —$N(R^b)$— groups;

Z is a group (A), (B), (C) or (D):

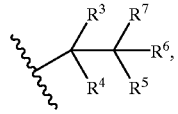

(A)

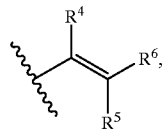

(B)

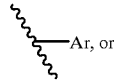

(C)

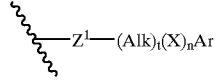

(D)

wherein

Ar is a monocyclic or bicyclic aryl group optionally containing one or more heteroatoms selected from oxygen, sulphur or nitrogen atoms;

$Z^1$ is a group —$NR^{12}C(O)$— [where $R^{12}$ is a hydrogen atom or an optionally substituted alkyl or (Alk)$_t$Ar group], —$C(O)NR^{12}$—, —$NR^{12}C(S)$—, —$C(S)NR^{12}$—, —C≡C—, —$NR^{12}SO_2$—, or —$SO_2NR^{12}$—;

Alk is an optionally substituted straight or branched alkyl chain optionally interrupted by an atom or group X;

t is zero or an integer of value 1, 2 or 3;

$R^3$ is a hydrogen or a fluorine atom or an optionally substituted straight or branched alkyl group or an $OR^{11}$ group [where $R^{11}$ is a hydrogen atom or an optionally substituted alkyl, alkenyl, alkoxyalkyl, alkanoyl, formyl, carboxamido or thiocarboxamido group];

$R^4$ is a hydrogen atom or an optionally substituted alkyl, $-CO_2R^8$, $-CSNR^9R^{10}$, $-CN$, $-CH_2CN$, or $-(CH_2)_tAr$ group where t is zero or an integer of value 1, 2 or 3 and Ar is a monocyclic or bicyclic aryl group optionally containing one or more heteroatoms selected from oxygen, sulphur or nitrogen atoms, provided that when L is a group of type (2) or (3) above then Z is a group of type (A) or type (B) in which $R^4$ is a $-(CH_2)_tAr$ group;

$R^5$ is a group $-(CH_2)_tAr$;

$R^6$ is a hydrogen or a fluorine atom, or an optionally substituted alkyl or $-CO_2R^8$, $-CONR^9R^{10}$, $-CSNR^9R^{10}$, $-CN$ or $-CH_2CN$ group;

$R^7$ is a hydrogen or a fluorine atom, an optionally substituted straight or branched alkyl group, or an $OR^c$ group where $R^c$ is a hydrogen atom or an optionally substituted alkyl or alkenyl group, alkoxyalkyl, alkanoyl, formyl, carboxamido or thiocarboxamido group; and the salts, solvates, hydrates, prodrugs and N-oxides thereof.

It will be appreciated that certain compounds of formula (1) may have one or more chiral centres, depending on the nature of the groups Alk, $R^1$, $R^2$, $R^3$, $R^4$, $R^5$, $R^6$ and $R^7$. Where one or more chiral centres is present, enantiomers or diastereomers may exist, and the invention is to be understood to extend to all such enantiomers, diastereomers and mixtures thereof, including racemates.

Compounds of formula (1) in which L is a $-C(R)=C(R^1)(R^2)$ group and/or Z is the group (B), may exist as geometric isomers depending on the nature of the groups R, $R^1$, $R^2$, $R^4$, $R^5$ and $R^6$, and the invention is to be understood to extend to all such isomers and mixtures thereof.

In the compounds of formula (1), when $=W-$ is $=C(Y)-$ and Y is a halogen atom Y may be for example a fluorine, chlorine, bromine or iodine atom.

When W in the compounds of formula (1) is a group $=C(Y)-$ and Y is $-XR^a$, $R^a$ may be, for example, a hydrogen atom or an optionally substituted straight or branched alkyl group, for example, an optionally substituted $C_{1-6}$alkyl group, such as a methyl, ethyl, n-propyl or i-propyl group. Optional substituents which may be present on $R^a$ groups include one or more halogen atoms, e.g. fluorine, or chlorine atoms. Particular $R^a$ groups include for example $-CH_2F$, $-CH_2Cl$, $-CHF_2$, $-CHCl_2$, $-CF_3$ or $-CCl_3$ groups.

When $=W-$ in the compounds of formula (1) is a group $=C(Y)-$ where $-Y$ is $-N(R^b)$, $=W-$ may be a $=C(NH_2)-$, $=C(NHCH_3)-$ or $=C(NHC_2H_5)-$ group.

In compounds of formula (1), X may be an oxygen or a sulphur atom, or a group $-S(O)-$, $-S(O)_2-$, $-NH-$ or $C_{1-6}$ alkylamino, for example a $C_{1-3}$ alkylamino, e.g. methylamino [$-N(CH_3)-$] or ethylamino [$-N(C_2H_5)-$] group.

Alkyl groups represented by Y, $R^1$, $R^2$ or $R^b$ in the compounds of formula (1) include optionally substituted straight or branched $C_{1-6}$ alkyl groups optionally interrupted by one or more X atoms or groups. Particular examples include $C_{1-3}$ alkyl groups such as methyl, ethyl, n-propyl or i-propyl groups. Optional substituents on these groups include one, two or three substituents selected from halogen atoms, e.g. fluorine, chlorine, bromine or iodine atoms, or hydroxyl or $C_{1-6}$ alkoxy e.g. $C_{1-3}$ alkoxy such as methoxy or ethoxy or $-CO_2R^8$, $-CONR^9R^{10}$, $-CSNR^9R^{11}$ or $-CN$ groups. Particular substituted alkyl groups include for example $-CH_2F$, $-CH_2Cl$, $-CHF_2$, $CHCl_2$, $-CF_3$ or $-CCl_3$ groups.

Alkenyl groups represented by $R^1$ or $R^2$ in the compounds of formula (1) include optionally substituted straight or branched $C_{2-6}$alkenyl groups optionally interrupted by one or more X atoms or groups. Particular examples include ethenyl, propen-1-yl and 2-methylpropen-1-yl groups. Optional substituents include those described above in relation to alkyl groups represented by the groups $R^1$ or $R^2$.

Alkynyl groups represented by $R^1$ or $R^2$ in compounds of formula (1) include optionally substituted straight or branched $C_{2-6}$alkynyl groups optionally interrupted by one or more X atoms or groups. Particular examples include ethynyl and propyn-1-yl groups. Optional substituents include those described above in relation to alkyl groups represented by the groups $R^1$ or $R^2$.

When $R^1$ or $R^2$ in compounds of formula (1) is an alkoxy or alkylthio group it may be for example an optionally substituted $C_{1-6}$alkoxy or $C_{1-6}$alkylthio group optionally interrupted by one or more X atoms or groups. Particular examples include $C_{1-3}$alkoxy, e.g. methoxy or ethoxy, or $C_{1-3}$alkylthio e.g. methylthio or ethylthio groups. Optional substituents include those described above in relation to alkyl groups represented by the groups $R^1$ or $R^2$.

When $R^1$ and $R^2$ together with the carbon atom to which they are attached in the compounds of formula (1) are linked to form a cycloalkyl or cycloalkenyl group, the group may be for example a $C_{3-8}$cycloalkyl group such as a cyclobutyl, cyclopentyl or cyclohexyl group or a $C_{3-8}$ cycloalkenyl group containing for example one or two double bonds such as a 2-cyclobuten-1-yl, 2-cyclopenten-1-yl, 3-cyclopenten-1-yl, 2,4-cyclopentadien-1-yl, 2-cyclohexen-1-yl, 3-cyclohexen-1-yl, 2,4-cyclohexadien-1-yl or 3,5-cyclohexadien-1-yl group, each cycloalkyl or cycloalkenyl group being optionally substituted by one, two or three substituents selected from halogen atoms, e.g. fluorine, chlorine, bromine or iodine atoms, straight or branched $C_{1-6}$alkyl e.g. $C_{1-3}$alkyl such as methyl or ethyl, hydroxyl or $C_{1-6}$alkoxy e.g. $C_{1-3}$alkoxy such as methoxy or ethoxy groups.

The linker atoms represented by the group $L^1$ include for example $-O-$ or $-S-$ atoms. Particular groups represented by the linker group $L^1$ are $-S(O)-$, $-S(O)_2-$, $-N(R^b)-$, $-C(O)-$, $-C(O)_2-$, $-C(S)-$, $-C(NR^b)-$ $-CON(R^b)-$, $-CSN(R^b)-$, $-N(R^b)CO-$, $-N(R^b)CS-$, $-SON(R^b)-$, $-SO_2N(R^b)-$, $-N(R^b)SO-$, $-N(R^b)SO_2-$, $-N(R^b)SO_2N(R^b)-$, $-N(R^b)SON(R^b)-$, $-N(R^b)CON(R^b)-$ or $-N(R^b)CSN(R^b)-$ groups. It will be appreciated that when the chain Alk is interrupted by two or more $L^1$ atoms or groups, such atoms or groups may be adjacent to one another, for example to form a group $-N(R^b)-C(NR^b)-N(R^b)-$ or $-O-CONH-$.

When L is a $-(X^a)_nAlk'Ar'$ or $Alk'X^aAr'$ group where Alk' is an alkylene chain L may be for example an optionally substituted straight or branched $C_{1-8}$alkylene chain optionally interrupted by one or more $L^1$ linker atoms or groups. Particular examples include $-CH_2Ar'$, $-(CH_2)_2Ar'$, $-OAr'$, $-SAr'$, $-N(R^b)Ar'$, $-C(O)Ar'$, $-C(S)Ar'$, $-CON(R^b)Ar'$, $-CSN(R^b)Ar'$, $-SOAr'$, $-SON(R^b)Ar'$, $-SO_2Ar'$, $-SO_2N(R^b)Ar'$, $OCH_2Ar'$, $-SCH_2Ar'$, $-N(R^b)CH_2Ar'$, $-CH_2OAr'$, $-CH_2SAr'$, $-CH_2N(R^b)Ar'$, $-CH_2C(O)Ar'$, $-CH_2C(S)Ar'$, $-CH_2CON(R^b)Ar'$, $-CH_2CSN(R^b)Ar'$, $-CH_2SOAr'$, $-CH_2SO_2Ar'$, $-(CH_2)_2OCH_2Ar'$, $-(CH_2)_2SCH_2Ar'$, $-(CH_2)_2SOCH_2Ar'$, $-(CH_2)_2SO_2CH_2Ar'$, $-(CH_2)_3Ar'$, $-O(CH_2)_3Ar'$, —S(CH$_2$)$_3$Ar', —N(R$^b$)(CH$_2$)$_3$Ar', —SO(CH$_2$)$_3$Ar', —SO$_2$(CH$_2$)$_3$Ar', —(CH$_2$)$_3$OAr', —(CH$_2$)$_3$SAr', —(CH$_2$)$_3$N(R$^b$)Ar', —(CH$_2$)$_3$SOAr' or —(CH$_2$)$_3$SO$_2$Ar' group. Optional substituents on these groups include those mentioned above in relation to the alkyl groups represented by Y, R$^1$, R$^2$ or R$^b$.

When L is a —(X$^a$)$_n$Alk'Ar' or Alk'X$^a$Ar' group where Alk' is an alkenylene chain it may be an optionally substituted straight or branched mono or polyunsaturated C$_{2-8}$alkenylene chain optionally interrupted by one or more L$^1$ linker atoms or groups. Particular examples include —(CH═CH)Ar', —CH═CH—CH$_2$Ar', —CH$_2$—CH═CHAr', —CH═CH—CH$_2$Ar', —OCH═CH—CH$_2$Ar', —OCH$_2$—CH═CHAr', —SCH═CH—CH$_2$Ar', —SCH$_2$—CH═CHAr', —N(R$^b$)CH═CH—CH$_2$Ar', —CH═CH—CH$_2$—OAr', —CH$_2$—CH═CH$_2$—OAr' or —CH═CH—CH═CHAr' group. Optional substituents on these groups include those mentioned above in relation to the alkyl groups represented by Y, R$^1$, R$^2$ or R$^b$.

When L is a (X$^a$)$_n$Alk'Ar' or Alk'X$^a$Ar' group where Alk' is an alkynylene chain, it may be an optionally substituted straight or branched mono or polyunsaturated C$_{2-8}$alkynylene chain optionally interrupted by one or more L$^1$ linker atoms or groups. Particular examples include —C≡CAr', —C≡C—CH$_2$Ar', —CH$_2$—C≡C—Ar', —OC≡C—CH$_2$Ar', —OCH$_2$—C≡CAr', —SC≡C—CH$_2$Ar', —SCH$_2$—C≡CAr', —N(R$^b$)C≡C—CH$_2$Ar', —N(R$^b$)CH$_2$—C≡CAr', —C≡C—CH$_2$OAr', —CH$_2$—C≡COAr', —C≡C—CH$_2$SAr', —CH$_2$—C≡CSAr', —CH$_2$—C≡CN(R$^b$)Ar' or —C≡C—CH$_2$N(R$^b$)Ar' group. Optional substituents on these groups include those mentioned above in relation to the alkyl groups represented by Y, R$^1$, R$^2$ or R$^b$.

When R$^1$ and R$^2$, together with the C atom to which they are attached are linked to form an optionally substituted heterocycloaliphatic group, and/or when Ar' is a heterocycloaliphatic group, the group may be for example an optionally substituted C$_{3-8}$ cycloalkyl or C$_{3-8}$ cycloalkenyl group containing one or more —O—, or —S— atoms, or —N(R$^b$)— groups such as a pyrrolidinyl, dioxolanyl, e.g. 1,3-dioxolanyl, imidazolidinyl, pyrazolidinyl, piperidinyl, 1,4-dioxanyl, morpholinyl, 1,4-dithianyl, thiomorpholinyl, piperazinyl, 1,3,5-trithianyl, 3-pyrrolinyl, 2-imidazolinyl, or 2-pyrazolinyl group. Optional substituents which may be present on such groups include one, two or three substituents selected from halogen atoms, e.g. fluorine, chlorine, bromine or iodine atoms, straight or branched C$_{1-6}$ alkyl e.g. C$_{1-3}$ alkyl such as methyl or ethyl, hydroxyl or C$_{1-6}$ alkoxy e.g. C$_{1-3}$ alkoxy such as methoxy or ethoxy groups.

Polycycloalkyl groups represented by R' in compounds of formula (1) include optionally substituted C$_{6-10}$ polycycloalkyl, e.g. bicycloalkyl or tricycloalkyl groups optionally containing one, two or more —O— or —S— atoms or —N(R$^b$)— groups. Polycycloalkenyl groups represented by Ar'include optionally substituted C$_{6-10}$ polycycloalkenyl, e.g. bicycloalkenyl or tricycloalkenyl groups optionally containing one, two or more—O— or —S— atoms or —N(R$^b$) groups. The degree of unsaturation of polycycloalkenyl groups may be varied widely and the term is to be understood to include groups with one, two, three or more —CH═CH— groups. Optional substituents which may be present on such groups include those mentioned above in relation to the Ar' group when Ar' is a hetero-cycloaliphatic group.

When the group R$^7$ in compounds of formula (1) is an OR$^c$ group it may be for example a hydroxyl group; or a group —OR$^c$ where R$^c$ is an optionally substituted straight or branched C$_{1-6}$alkyl group, e.g. a C$_{1-3}$alkyl group such as a methyl or ethyl group, a C$_{2-6}$alkenyl group such as an ethenyl or 2-propen-1-yl group, a C$_{1-3}$alkoxyC$_{1-3}$alkyl group such as a methoxymethyl, ethoxymethyl or ethoxyethyl group, a C$_{1-6}$alkanoyl, e.g. C$_{1-3}$alkanoyl group such as an acetyl group, or a formyl [HC(O)—], carboxamido (CONR$^{13}$R$^{13a}$) or thiocarboxamido (CSNR$^{13}$R$^{13a}$) group, where R$^{13}$ and R$^{13a}$ in each instance may be the same or different and is each a hydrogen atom or an optionally substituted straight or branched C$_{1-6}$alkyl, e.g. C$_{1-3}$alkyl group such as methyl or ethyl group. Optional substituents which may be present on such R$^c$, R$^{13}$ or R$^{13a}$ groups include those described below in relation to the alkyl groups R$^3$, R$^4$, R$^6$, R$^7$ and R$^{12}$.

Alkyl groups represented by R$^3$, R$^4$, R$^6$, R$^7$ or R$^{12}$ in compounds of formula (1) include optionally substituted straight or branched C$_{1-6}$ alkyl groups, e.g. C$_{1-3}$ alkyl groups such as methyl, ethyl, n-propyl or i-propyl groups. Optional substituents which may be present on these groups include one or more halogen atoms, e.g. fluorine, chlorine, bromine or iodine atoms, or hydroxyl or C$_{1-6}$alkoxy e.g. C$_{1-3}$alkoxy such as methoxy or ethoxy groups.

When R$^1$, R$^2$, R$^4$ or R$^6$ is a —CO$_2$R$^8$, —CONR$^9$R$^{10}$ or CSNR$^9$R$^{10}$ group it may be for example a —CO$_2$H, —CONH$_2$ or —CSNH$_2$ group or a group —CO$_2$R$^8$, —CONR$^9$R$^{10}$, —CSNR$^9$R$^{10}$, —CONHR$^{10}$, or —CSNHR$^{10}$ where R$^8$, R$^9$ and R$^{10}$ where present is a C$_{1-3}$alkyl group such as methyl or ethyl group, a C$_{6-12}$aryl group, for example an optionally substituted phenyl, or a 1- or 2-naphthyl group, or a C$_{6-12}$aryl C$_{1-3}$alkyl group such as an optionally substituted benzyl or phenethyl group. Optional substituents which may be present on these aryl groups include R$^{14}$ substituents discussed below in relation to the group Ar.

When the chain Alk is present in compounds of formula (1) it may be an optionally subtituted straight or branched C$_{1-3}$alkylene chain optionally interrupted by an atom or group X. Particular examples include —CH$_2$—, —(CH$_2$)$_2$—, —(CH$_2$)$_3$—, —CH$_2$OCH$_2$—, —CH$_2$SCH$_2$—, or —CH$_2$N(R$^b$)CH$_2$—, e.g. —CH$_2$NHCH$_2$— or —CH$_2$N(CH$_3$)CH$_2$— chains. Optional substituents include those described in relation to the alkyl groups represented by R$^3$, R$^4$, R$^6$, R$^7$ and R$^{12}$.

In the compounds of formula (1) when the group —(Alk)$_t$(X)$_n$Ar is present it may be a group —Ar, —CH$_2$Ar, —(CH$_2$)$_2$Ar, —(CH$_2$)$_3$Ar, —CH$_2$OAr, —CH$_2$OCH$_2$Ar, —CH$_2$N(R$^b$)Ar or —CH$_2$N(R$^b$)CH$_2$Ar group.

Monocyclic or bicyclic aryl groups represented by the group Ar, Ar', or R' in compounds of formula (1) include for example C$_{6-12}$ optionally substituted aryl groups, for example optionally substituted phenyl, 1- or 2-naphthyl, indenyl or isoindenyl groups.

When the monocyclic or bicyclic aryl group Ar, Ar' or R' contains one or more heteroatoms it may be for example a C$_{5-10}$ optionally substituted heteroaryl group containing for example one, two, three or four heteroatoms selected from oxygen, sulphur or nitrogen atoms. In general, Ar heteroaryl groups may be for example monocyclic or bicyclic heteroaryl groups. Monocyclic heteroaryl groups include for example five- or six-membered heteroaryl groups containing one, two, three or four heteroatoms selected from oxygen, sulphur or nitrogen atoms. Bicyclic heteroaryl groups include for example nine- or ten-membered heteroaryl groups containing one, two or more heteroatoms selected from oxygen, sulphur or nitrogen atoms.

Examples of heteroaryl groups represented by Ar, Ar' or R' include pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, isobenzothienyl, indolyl, isoindolyl, benzimidazolyl, benzothiazolyl, benzoxazolyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl and 5,6,7,8-tetrahydroisoquinolinyl. Example of bicyclic heteroaryl groups include quinolinyl or isoquinolinyl groups.

The heteroaryl group represented by Ar, Ar' or R' may be attached to the remainder of the molecule of formula (1) through any ring carbon or heteroatom as appropriate. Thus, for example, when the group Ar or Ar' is a pyridyl group it may be a 2-pyridyl, 3-pyridyl or 4-pyridyl group. When it is a thienyl group it may be a 2-thienyl or 3-thienyl group, and, similarly, when it is a furyl group it may be a 2-furyl or 3-furyl group. In another example, when the group Ar is a quinolinyl group it may be a 2-, 3-, 4-, 5-, 6-, 7- or 8-quinolinyl and when it is an isoquinolinyl, it may be a 1-, 3-, 4-, 5-, 6-, 7- or 8-isoquinolinyl group.

When in compounds of formula (1) the Ar, Ar' or R' group is a nitrogen-containing heterocycle it may be possible to form quaternary salts, for example N-alkyl quaternary salts and the invention is to be understood to extend to such salts. Thus for example when the group Ar is a pyridyl group, pyridinium salts may be formed, for example N-alkylpyridinium salts such as N-methylpyridinium.

The aryl or heteroaryl groups represented by Ar, Ar' or R', in compounds of formula (1) may each optionally be substituted by one, two, three or more substituents [$R^{14}$]. The substituent $R^{14}$ may be selected from an atom or group $R^{15}$ or —$Alk^1(R^{15})_m$ wherein $R^{15}$ is a halogen atom, or an amino (—$NH_2$), substituted amino, nitro, cyano, hydroxyl (—OH), substituted hydroxyl, cycloalkoxy, cycloaliphatic, formyl [HC(O)—], carboxyl (—$CO_2H$), esterified carboxyl, thiol (—SH), substituted thiol, —C(O)R" [where R" is a group $Alk^1$ where $Alk^1$ is a straight or branched $C_{1-6}$ alkylene, $C_{2-6}$alkenylene, or $C_{2-6}$alkynylene chain optionally interrupted by one, two, or three —O—, or —S— atoms or —S(O)$_z$—, (where z is an integer 1 or 2) or —N($R^b$)— groups; or is a group Ar" (where Ar" is as defined for Ar), —$SO_3H$, —$SO_2R"$, —$SO_2NH_2$, —$SO_2NHR"$ —$SO_2N[R"]_2$, —$CONH_2$, —CONHR" —CON[R"]$_2$, —$NHSO_2H$, —N(R")$SO_2H$, —$NHSO_2R"$, —NR"$SO_2R"$, —N[$SO_2R"$]$_2$, —$NHSO_2NH_2$, —NR"$SO_2NH_2$, —$NHSO_2NHR"$, —NR"$SO_2NHR"$, —NR"$SO_2NHR"$, —$NHSO_2N[R"]_2$, —N(R")$SO_2N[R"]_2$, —NHC(O)R", —NR"C(O)R", —N[C(O)R"]$_2$, —NHC(O)H, —NR"C(O)H, —NHC(O)OR", —NR"C(O)OR", —NHC(O)OH, —NR"C(O)OH, —$NHCONH_2$, —NHCONHR", —NHCON[R"]$_2$, —NR"CON[R"]$_2$, —C(S)R", —C(S)NH$_2$, —C(S)NHR", —C(S)N[R"]$_2$, —NHC(S)R", —NR"C(S)R", —N[[C(S)R"]$_2$, —NHC(S)H, —NR"C(S)H, —NHC(S)NH$_2$, —NHC(S)NHR", —NHC(S)N[R"]$_2$, —NR"C(S)N[R"]$_2$, —Ar" or —XAr" group; and m is zero or an integer 1, 2 or 3.

When in the group —$Alk^1(R^{15})_m$ m is an integer 1, 2 or 3, it is to be understood that the substituent or substituents $R^{15}$ may be present on any suitable carbon atom in —$Alk^1$. Where more than one $R^{15}$ substituent is present these may be the same or different and may be present on the same or different carbon atom in $Alk^1$. Clearly, when m is zero and no substituent $R^{15}$ is present or when $Alk^1$ forms part of a group such as —$SO_2Alk^1$ the alkylene, alkenylene or alkynylene chain represented by $Alk^1$ becomes an alkyl, alkenyl or alkynyl group.

When $R^{15}$ is a substituted amino group it may be a group —NH[$Alk^1(R^{15a})_m$] [where $Alk^1$ and m are as defined above and $R^{15a}$ is as defined above for $R^{15}$ but is not a substituted amino, a substituted hydroxyl or a substituted thiol group] or a group —N[$Alk^1(R^{15a})_m$]$_2$ wherein each —$Alk^1(R^{15a})_m$ group is the same or different.

When $R^{15}$ is a halogen atom it may be for example a fluorine, chlorine, bromine, or iodine atom.

When $R^{15}$ is a cycloalkoxy group it may be for example a $C_{5-7}$cycloalkoxy group such as a cyclopentyloxy or cyclohexyloxy group.

When $R^{15}$ is a substituted hydroxyl or substituted thiol group it may be a group —$OAlk^1(R^{15a})_m$ or —$SAlk^1(R^{15a})_m$ respectively, where $Alk^1$, $R^{15a}$ and m are as just defined.

Esterified carboxyl groups represented by the group $R^{15}$ include groups of formula —$CO_2Alk^2$ wherein $Alk^2$ is a straight or branched, optionally substituted $C_{1-8}$alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxyethyl, 1-naphthyloxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the $Alk^2$ group include $R^{14}$ substituents described above.

When the group $R^{15}$ in compounds of formulae (1) and (2) is an optionally substituted $C_{3-9}$cycloaliphatic group, it may be a $C_{3-9}$cycloalkyl or $C_{3-9}$cycloalkenyl group such as a $C_{5-7}$cycloalkyl or $C_{5-7}$cycloalkenyl group, containing 1, 2, 3 or more heteroatoms selected from oxygen, sulphur or nitrogen atoms. Particular examples of such $R^{15}$ groups include pyrrolyl, e.g. 2H-pyrrolyl, pyrrolinyl, e.g. 2- or 3-pyrrolinyl, pyrrolidinyl, 1,3-dioxolanyl, imidazolinyl, e.g. 2-imidazolinyl, imidazolidinyl, pyrazolinyl, e.g. 2-pyrazolinyl, pyrazolidinyl, pyranyl, e.g. 2- or 4-pyranyl, piperidinyl, 1,4-dioxanyl, morpholinyl, 1,4-dithianyl, thiomorpholinyl, piperazinyl, 1,3,5-trithianyl, 3H-pyrrolyl, 2H-imidazolyl, dithiolyl, e.g. 1,2- or 1,3-dithiolyl, oxathiolyl, e.g. 3H-1-2 or 1,3-oxathiolyl, 5H-1,2,5-oxathiozolyl, 1,3-dioxinyl, oxazinyl, e.g. 2H-1,3-, 6H-1,3-, 6H-1,2-, 1,4-2H-1,2- or 4H-1,4-oxazinyl, 1,2,5-oxathiazinyl, isoxazinyl, e.g. -o- or p-isoxazinyl, oxathiazinyl, e.g. 1,2,5-, 1,2,6-oxathiazinyl, 1,3,5,2-oxadiazinyl, or 1,2,4-diazepinyl groups. Optional substituents which may be present on such groups include those substituents discussed above in relation to the group Ar' where Ar' is a heterocycloaliphatic group.

It will be appreciated that the group Ar, Ar' or R' may be attached to the remainder of the molecule of formula (1) through either a ring carbon atom or heteroatom.

Particular examples of the group $Alk^1$ when present include methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S— atoms or —S(O)—, —S(O)$_2$— or —N($R^b$)— groups.

Particularly useful atoms or groups represented by $R^{14}$ include fluorine, chlorine, bromine or iodine atoms, or $C_{1-6}$alkyl, e.g. methyl or ethyl, $C_{1-6}$alkylamino, e.g. methylamino or ethylamino, $C_{1-6}$ hydroxyalkyl, e.g. hydroxymethyl or hydroxyethyl, $C_{1-6}$alkylthiol e.g. methylthiol or ethylthiol, $C_{1-6}$alkoxy, e.g. methoxy or ethoxy, $C_{5-7}$cycloalkyl e.g. cyclopentyl, $C_{5-7}$ cycloalkoxy, e.g. cyclopentyloxy, halo$C_{1-6}$alkyl, e.g. trifluoromethyl, $C_{1-6}$ alkylamino, e.g. methylamino or ethylamino, amino (—$NH_2$), amino$C_{1-6}$alkyl, e.g. aminomethyl or aminoethyl, $C_{1-6}$dialkylamino, e.g. dimethylamino or diethylamino, nitro, cyano, hydroxyl (—OH), formyl [HC(O)—], carboxyl (—$CO_2H$), —$CO_2Alk^2$ [where $Alk^2$ is as defined above], $C_{1-6}$ alkanoyl e.g. acetyl, thiol (—SH), thio$C_{1-6}$alkyl, e.g. thiomethyl or thioethyl, sulphonyl (—$SO_3H$), $C_{1-6}$alkylsulphonyl, e.g. methylsulphonyl, aminosulphonyl (—$SO_2NH_2$), $C_{1-6}$alkylaminosulphonyl, e.g. methylaminosulphonyl or ethyl-aminosulphonyl, $C_{1-6}$dialkylaminosulphonyl, e.g. dimethylaminosulphonyl or diethylaminosulphonyl, phenylaminosulphonyl, carboxamido (—$CONH_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, phenylaminocarbonyl, sulphonylamino (—$NHSO_2H$), $C_{1-6}$alkylsulphonylamino, e.g. methylsulphonylamino or ethylsulphonylamino, $C_{1-6}$ dialkylsulphonylamino, e.g. dimethylsulphonylamino or diethylsulphonylamino, aminosulphonylamino (—$NHSO_2NH_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, phenylaminosulphonylamino, $C_{1-6}$alkanoylamino, e.g. acetylamino, $C_{1-6}$alkanoylamino$C_{1-6}$alkyl, e.g. acetylaminomethyl or $C_{1-6}$ alkoxycarbonylamino, e.g. methoxycarbonylamino, ethoxycarbonylamino or t-butoxycarbonylamino, thiocarboxamido (—$CSNH_2$), $C_{1-6}$ alkylaminothiocarbonyl, e.g. methylaminothiocarbonyl or ethylaminothiocarbonyl, $C_{1-6}$dialkylaminothiocarbonyl, e.g. dimethylaminothiocarbonyl or diethylaminothiocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, aminothiocarbonylamino, $C_{1-6}$alkylaminothiocarbonylamino, e.g. methylaminothiocarbonylamino or ethylaminothiocarbonylamino, $C_{1-6}$ dialkylaminothiocarbonylamino, e.g. dimethylaminothiocarbonylamino, or diethylaminothiocarbonylamino, aminocarbonyl$C_{1-6}$alkylamino, e.g. aminocarbonylmethylamino or aminocarbonylethylamino, aminothiocarbonyl$C_{1-6}$alkylamino e.g. aminothiocarbonylmethylamino or aminothiocarbonylethylamino, formylamino$C_{1-6}$ alkylsulphonylamino, e.g. formylaminomethylsulphonylamino or formylaminoethylsulphonylamino, thioformylamino$C_{1-6}$alkylsulphonylamino, e.g. thioformylaminomethylsulphonylamino or thioformylethylsulphonylamino, $C_{1-6}$acylaminosulphonylamino, e.g. acetylaminosulphonylamino, $C_{1-6}$thioacylaminosulphonylamino, e.g. thioacetylaminosulphonylamino groups, —Ar", e.g. phenyl, —XAr" e.g. phenoxy, or —$Alk^1Ar$" e.g. benzyl or phenethyl groups.

Where desired, two $R^{14}$ substituents may be linked together to form a cyclic group such as a cyclic ether, e.g. a $C_{2-6}$alkylenedioxy group such as ethylenedioxy.

It will be appreciated that where two or more $R^{14}$ substituents are present, these need not necessarily be the same atoms and/or groups. The $R^{14}$ substituents may be present at any ring carbon atom away from that attached to the rest of the molecule of formula (1). Thus, for example, in phenyl groups represented by Ar any substituent may be present at the 2-, 3-, 4-, 5- or 6-positions relative to the ring carbon atom attached to the remainder of the molecule.

Particular examples of the chain $Z^1$ in compounds of formula (1) include —NHCO—, —CONH—, —NHCS—, —CSNH—, —$NHSO_2$—, —$SO_2NH$— and —C=C—.

In the compounds of formula (1), when an ester group is present, for example a group —$CO_2R^8$ or —$CO_2Alk^2$ this may advantageously be a metabolically labile ester.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Prodrugs of compounds of formula (1) include those compounds, for example esters, alcohols or aminos, which are convertible in vivo by metabolic means, e.g. by hydrolysis, reduction, oxidation or trans-esterification, to compounds of formula (1).

Particularly useful salts of compounds according to the invention include pharmaceutically acceptable salts, especially acid addition pharmaceutically acceptable salts.

In the compounds of formula (1) the group =W— is preferably a =C(Y)— group. In compounds of this type Y is preferably a —$XR^a$ group where X is —O— and $R^a$ is an optionally substituted ethyl group or, especially, an optionally substituted methyl group. Especially useful substituents which may be present on $R^a$ groups include one, two or three fluorine or chlorine atoms.

The group L in compounds of formula (1) is preferably a —CH=C($R^1$)($R^2$) group. In compounds of this type $R^1$ and $R^2$ are preferably linked together with the C atom to which they are attached to form an optionally substituted cycloalkyl or cycloalkenyl group, especially a substituted cyclopentyl or cyclohexyl or, especially, a cyclopentyl or cyclohexyl group.

In the compounds of formula (1) where Z is the group (A), one preferred group of compounds are those where the group $R^3$ is a hydrogen atom; the group $R^6$ is a methyl group, or especially a hydrogen atom; the group $R^7$ is a methyl group, or especially a hydrogen atom; and $R^4$ and $R^5$ are as defined for formula (1). In compounds of this type $R^6$ and $R^7$ in one preference, is each a methyl group; in another preference, one of $R^6$ or $R^7$ is a methyl group and the other is a hydrogen atom, in general, however, $R^6$ and $R^7$ is each especially a hydrogen atom.

The groups $R^4$ and $R^5$ when present in compounds of formula (1) are each, independently, preferably a —$CH_2Ar$ group, or, especially, an —Ar group. Particularly useful $R^4$ or $R^5$ groups of this type include those groups in which Ar is a monocyclic aryl group optionally containing one or more heteroatoms selected from oxygen, sulphur, or, in particular, nitrogen atoms, and optionally substituted by one, two, three or more $R^{14}$ substituents. In these compounds, when the group represented by Ar is a heteroaryl group it is preferably a nitrogen-containing monocyclic heteroaryl group, especially a six-membered nitrogen-containing heteroaryl group. Thus, in one preferred example, the groups $R^4$ and $R^5$ may each be a six-membered nitrogen-containing heteroaryl group. In another preferred example $R^4$ may be a monocyclic aryl group or a monocyclic or bicyclic heteroaryl group containing one or more oxygen, sulphur or nitrogen atom and $R^5$ may be a six-membered nitrogen-containing heteroaryl group. In these examples, the six-membered nitrogen-containing heteroaryl group may be an optionally substituted pyridyl, pyridazinyl, pyrimidinyl, pyrazinyl or imidazolyl group. Particular examples include optionally substituted 2-pyridyl, 3-pyridyl, 5-imidazolyl, or, especially, 4-pyridyl, 3-pyridazinyl, 4-pyridazinyl, 5-pyridazinyl, 2-pyrimidinyl, 4-pyrimidinyl, 5-pyrimidinyl, 2-pyrazinyl or 3-pyrazinyl. The monocyclic aryl group may be a phenyl group or a substituted phenyl group, and the monocyclic or bicyclic heteroaryl group containing one or more oxygen, sulphur or nitrogen atom may be an optionally substituted 2-furyl, 3-furyl, 2-thienyl, 3-thienyl, 2-thiazolyl, 2-benzo(b)thiophenyl, 2-benzo(b)furyl or 4-isoquinolinyl group.

One particularly useful group of compounds of formula (1) when Z is a group (A) or (B) is that wherein $R^4$ and $R^5$ is each a pyridyl or, especially, a monosubstituted pyridyl, or preferably a disubstituted pyridyl group, or $R^4$ is a phenyl, thienyl or furyl, or substituted phenyl, thienyl or furyl group and $R^5$ is a pyridyl or, especially a monosubstituted pyridyl, or preferably a disubstituted pyridyl group.

In this particular group of compounds and also in general in compounds of formula (1) when $R^4$ and/or $R^5$ is a substituted phenyl group it may be for example a mono-, di- or trisubstituted phenyl group in which the substituent is an atom or group $R^{14}$ as defined above. When the $R^4$ and/or $R^5$ group is a monosubstituted phenyl group the substituent may be in the 2-, or preferably 3-, or especially 4-position relative to the ring carbon atom attached to the remainder of the molecule. When the $R^4$ and/or $R^5$ group is a disubstituted phenyl group, the substituents may be in the 2,6 position relative to the ring carbon atom attached to the remainder of the molecule.

When in compounds of formula (1) $R^4$ and/or $R^5$ is a substituted pyridyl group it may be for example a mono- or disubstituted pyridyl group, such as a mono- or disubstituted 2-pyridyl, 3-pyridyl or especially 4-pyridyl group substituted by one or two atoms or groups $R^{14}$ as defined above, in particular one or two halogen atoms such as fluorine or chlorine atoms, or methyl, methoxy, hydroxyl or nitro groups. Particularly useful pyridyl groups of these types are 3-monosubstituted-4-pyridyl or 3,5-disubstituted-4-pyridyl, or 2- or 4-monosubstituted-3-pyridyl or 2,4-disubstituted-3-pyridyl groups.

Other particularly useful groups of compounds of formula (1) where Z is the group (B), include those where $R^4$ is a —$CH_3$ group or a hydrogen atom; $R^5$ is a hydrogen atom, a —CN or a —$CH_3$ group; $R^6$ is as just described for $R^4$ and $R^5$ in the compounds of formula (1) where Z is the group (A).

Another particularly useful group of compounds of formula (1) when Z is a group (C) is that wherein Ar is a phenyl, naphthyl, pyrrolyl, furyl, thienyl, imidazolyl, oxazolyl, thiazolyl, pyrazolyl, pyridyl, pyrimidinyl, pyridazinyl, quinolinyl, isoquinolinyl, 5,6,7,8-tetrahydroquinolinyl or 5,6,7,8-tetrahydro-isoquinolinyl group. In compounds of this type when Ar is a quinolinyl group it may be for example a mono- or disubstituted quinolinyl group such as a 2-monosubstituted-4-quinolinyl group; when it is a pyridyl group, it may be an optionally substituted 3- or 4-pyridyl, e.g. a 2,3,5,6-tetrasubstituted-4-pyridyl or 2,4,6-trisubstituted-3-pyridyl group; when it is a pyrimidinyl group, it may be for example a 5-pyrimidinyl group or a 2-substituted 5-pyrimidinyl group; and when it is an isoquinolinyl group, it may be a 4-isoquinolinyl group.

Other especially useful groups of compounds of formula (1) include those where Z is a group (D) in which (1) —$Z^1$— is a —C(O)NR$^{12}$— group, where $R^{12}$ is a hydrogen atom. In compounds of this type, t is preferably zero and Ar is a 2-nitrophenyl or 4-(3,5-dichloro)pyridyl group, or (2) those where —$Z^1$— is a —NR$^{12}$C(O)— group, where $R^{12}$ is a hydrogen atom, t is zero and Ar is a 4-pyridyl or 4-(3,5-dichloro)pyridyl, benzyl or 2-methylbenzoate group, or t is an integer of value 1 and Ar is a 2- or 3-nitrophenyl, phenyl or 2-methylphenyl group.

A particularly useful group of compounds of formula (1) has the formula (2):

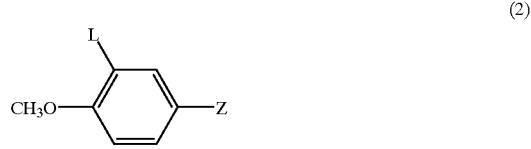

where (1) —L is a —CH═C(R$^1$)(R$^2$) or —CH$_2$CH(R$^1$)(R$^2$) group where $R^1$ and $R^2$ are linked together with the carbon atom to which they are attached to form a cycloalkyl group; or (2) L is a group —OAlkAr' where Alk is a $C_{1-6}$alkylene chain and Ar' is a monocyclic aryl or heteroaryl group. Particular examples of such L groups include benzyloxy, thienyloxy or phenylpentyloxy groups; or (3) L is a group OR' where R' is an optionally substituted polycyloalkyl or polycycloalkyl group or is as described above for Ar'. Preferred examples of such R' groups include optionally substituted bicycylo[2.2.1]heptyl or bicyclo[2.2.1]heptenyl group. In particular R' is a bicyclo[2.2.1]hept-2-yl group; and Z is as defined for formula (1); and the salts, solvates, hydrates, prodrugs and N-oxides thereof.

In compounds of formula (2) where $R^3$, $R^6$ or $R^7$ is present it is each preferably a hydrogen atom.

A particularly useful group of compounds according to the invention has the formula (2) wherein L is a OR' group and Z is the group (A). In this particular group of compounds $R^3$, $R^6$ and $R^7$ is each a hydrogen atom and $R^4$ and $R^5$ are as defined for compounds of formula (1) and the salts, solvates, hydrates and N-oxides thereof. Compounds of this type in which R' is a bicyclo[2.2.1]heptyl, particularly a bicyclo[2.2.1]hept-2-yl group are particularly useful. In this group of compounds, $R^4$ is preferably a monocyclic aryl group, particularly a phenyl or substituted phenyl group or $R^4$ is a six-membered nitrogen-containing monocyclic heteroaryl group, particularly a pyridyl or substituted pyridyl group and $R^5$ is a six-membered nitrogen-containing monocyclic heteroaryl group, especially a pyridyl or substituted pyridyl group, in particular a 4-pyridyl or substituted 4-pyridyl group.

Other particularly useful groups of compounds of formulae (1) or (2) where L is a group —C(R)═C(R$^1$)(R$^2$) or —(X$^a$)$_n$Alk'Ar' and Z is the group (B), include those where $R^4$ is a —$CH_3$ group or a hydrogen atom; $R^5$ is a hydrogen atom, a —CN or a —$CH_3$ group; $R^6$ is as just described for $R^4$ and $R^5$ in the compounds of formulae (1) or (2) where Z is the group (A).

Particular compounds according to the invention are:

(2R)-4-{2-[3-((2RS)-exo-Bicyclo[2.2.1]hept-2-yloxy)-4-methoxyphenyl]-2-phenylethyl}pyridine;

(±)-4-[2-(3-Benzyloxy-4-methoxyphenyl)-2-phenylethyl]pyridine;

(±)-4-{2-[4-Methoxy-3-(3-thienyloxy)phenyl]-2-phenylethyl}pyridine;

(±)-4-[2-(3-Cyclopentylidenyl-4-methoxyphenyl)-2-phenylethyl]pyridine;

(±)-4-[2-(3-Cyclohexylidenyl-4-methoxyphenyl)-2-phenylethyl]pyridine;

(E,Z)-3-(3-Cyclopentylidenyl-4-methoxyphenyl)-2-(2,6-dichlorophenyl) propenenitrile;

(E,Z)-3-(3-Cyclopentylidenyl-4-methoxyphenyl)-2-(2,6-difluorophenyl) propenenitrile;

(E,Z)-4-[2-(3-Cyclopentylidenyl-4-methoxyphenyl) ethenyl]-3,5-dichloropyridine;

3-(3-Cyclopentylidenyl-4-methoxyphenyl)pyridine;

5-(3-Cyclopentylidenyl-4-methoxyphenyl)pyrimidine;

4-(3-Cyclopentylidenyl-4-methoxyphenyl)nitrobenzene;

3-(3-Cyclopentylmethyl-4-methoxyphenyl)pyridine;

N-(3-Cyclopentylidenyl-4-methoxyphenyl)-3,5-dichloro-4-pyridenecarboxamide;

4-[2-(3-Cyclopentylidenyl-4-methoxyphenyl)ethyl]pyridine;

N-{4-[2-(3-Cyclopentylidenyl-4-methoxyphenyl)ethyl]-3-pyridyl}phenylsulphonamide;

3-Cyclopentylidenyl-4-methoxy-N-(2-nitrobenzoyl)aniline;

N-(3-Cyclopentylidenyl-4-methoxyphenyl)-4-pyridinecarboxamide;

N-Phenyl-3-cyclopentylidenyl-4-methoxybenzamide;

N-(2-Nitrophenyl)-3-cyclopentylidenyl-4-methoxybenzamide;

N-(3,5-Dichloropyrid-4-yl)-3-cyclopentylidenyl-4-methoxybenzamide;

and the salts, solvates, hydrates, prodrugs and N-oxides thereof.

Compounds according to the invention are selective and potent inhibitors of PDE IV. The ability of the compounds to act in this way may be simply determined by the tests described in the Examples hereinafter. Particular uses to which the compounds of the invention may be put include the prophylaxis and treatment of asthma, especially inflamed lung associated with asthma, cystic fibrosis, or in the treatment of inflammatory airway disease, chronic bronchitis, eosinophilic granuloma, psoriasis and other benign and malignant proliferative skin diseases, endotoxic shock, septic shock, ulcerative colitis, Crohn's disease, reperfusion injury of the myocardium and brain, inflammatory arthritis, chronic glomerulonephritis, atopic dermatitis, urticaria, adult respiratory distress syndrome, diabetes insipidus, allergic rhinitis, allergic conjunctivitis, vernal conjunctivitis, arterial restenosis and artherosclerosis.

Compounds of the invention may also suppress neurogenic inflammation through elevation of cAMP in sensory neurones. They are, therefore, analgesic, anti-tussive and anti-hyperalgesic in inflammatory diseases associated with irritation and pain.

Compounds according to the invention may also elevate cAMP in lymphocytes and thereby suppress unwanted lymphocyte activation in immune-based diseases such as rheumatoid arthritis, ankylosing spondylitis, transplant rejection and graft versus host disease.

Compounds according to the invention may also reduce gastric acid secretion and therefore can be used to treat conditions associated with hypersecretion.

Compounds of the invention may suppress cytokine synthesis by inflammatory cells in response to immune or infectious stimulation. They are, therefore, useful in the treatment of bacterial, fungal or viral induced sepsis and septic shock in which cytokines such as tumour necrosis factor (TNF) are key mediators. Also compounds of the invention may suppress inflammation and pyrexia due to cytokines and are, therefore, useful in the treatment of inflammation and cytokine-mediated chronic tissue degeneration which occurs in diseases such as rheumatoid or osteoarthritis.

Over-production of cytokines such as TNF in bacterial, fungal or viral infections or in diseases such as cancer, leads to cachexia and muscle wasting. Compounds of the invention may ameliorate these symptoms with a consequent enhancement of quality of life.

Compounds of the invention may also elevate cAMP in certain areas of the brain and thereby counteract depression and memory impairment.

Compounds of the invention may suppress cell proliferation in certain tumour cells and can be used, therefore, to prevent tumour growth and invasion of normal tissues.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of formulae (1) and (2) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formulae (1) and (2) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular inflammatory condition will vary depending on the compound chosen, and the condition of the patient to be treated. In general, however, daily dosages may range from around 100 ng/kg to 100 mg/kg, e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds according to the invention may be prepared by the following processes. The symbols W, L, Z, X, $R^1$, $R^2$, $R^3$, $R^4$, $R^5$, $R^6$, and $R^7$ when used in the formulae below are to be understood to represent those groups described above in relation to formula (1) unless otherwise indicated. In the reactions described below it may be necessary to protect reactive functional groups, for example hydroxy, amino, thio, carboxy or aldehyde groups, where these are desired in the final product, to avoid their unwanted participation in the reactions. Conventional protecting groups may be used in accordance with standard practice [see, for example, Green, T. W. in "Protective Groups in Organic Synthesis" John Wiley and Sons, 1981].

Thus, according to a further aspect of the invention, compounds of general formula (1) where L is $X^aAlk'Ar'$, $Alk'X^aAr'$ or $X^aR'$ may be prepared by coupling an intermediate of formula (3)

(3)

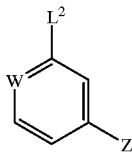

a) where $L^2$ is a group —$X^aH$ with a reagent $L^3Alk'Ar'$, or $L^3R'$ where $L^3$ is a leaving group; or b) where $L^2$ is a group —$Alk'L^3$ with a reagent $Ar'X^aH$.

Leaving groups represented by $L^3$ include halogen atoms such as iodine, chlorine or bromine atoms, sulphonyloxy groups such as arylsulpyhonyloxy groups, e.g. p-toluenesulphonyloxy or hydroxyl groups.

The coupling reaction may be carried out in the presence of a base, e.g. an inorganic base such as a carbonate, e.g. caesium or potassium carbonate, an alkoxide, e.g. potassium t-butoxide, or a hydride, e.g. sodium hydride, in a dipolar aprotic solvent such as an amide, e.g. a substituted amide, such as dimethylformamide or an ether, e.g. diethylether or a cyclic ether such as tetrahydrofuran or halogenated solvents, such as dichloromethane. The temperature of the reaction mixture may vary from ambient temperature or above, e.g. around 40° C. to the reflux temperature. Where necessary, an activator may be used, such as diethyl-, diisopropyl-, or dimethylazodicarboxylate, in the presence of a phosphine, such as triphenylphosphine and a base, such as an amine, e.g. triethylamine.

Intermediates of formula (3) where $L^2$ is a group —$Alk'L^3$ wherein $L^3$ is a halogen atom may be prepared by reaction of an intermediate of formula (3) wherein $Alk'L^3$ is a —$Alk'OH$ group with a halogenating agent, such as an inorganic acid halide e.g. thienylchloride, or an anhydride such as an arylsulphonic anhydride, e.g. p.toluenesulphonic anhydride, using conventional procedures.

Intermediates of formula (3) where $L^2$ is a group —$X^aH$ may be prepared by deprotection of a protected compound of formula (4)

(4)

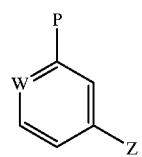

where P is a hydroxy, thio, or amino protecting group. Examples of hydroxy protecting groups include, for example ether groups, such as a cyclopentyloxy group. The deprotection reaction may take place in an aqueous solvent, such as an aqueous ether, e.g. dioxane-water, in the presence of an acid, e.g. sulphuric acid at an elevated temperature. e.g. around 90° C. Another example of protecting group P include t-butyldimethylsilyloxy group which can be cleaved by treatment with tetrabutylammonium fluoride to regenerate the free hydroxy group.

Intermediates of formula (3) where Z is a group (A) in which $R^3$ is a hydroxyl group and $R^7$ is a hydrogen atom may be prepared by reacting a ketone of formula (5)

(5)

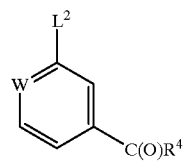

with an organometallic reagent $R^5R^6CHM$, where M is a metal atom.

Metal atoms represented by Z include, for example, a lithium atom.

The reaction may be performed in a solvent such as an ether, e.g. a cyclic ether such as tetrahydrofuran, at a low temperature e.g. around −70° C. to ambient temperature. This reaction is particularly suitable for the preparation of compounds of formula (3) wherein $R^5$ is an electron deficient group such as a 2- or 4-pyridyl group.

Reagents $R^5R^6$CHM are either known compounds or may be prepared, preferably in situ during the above process, by reaction of a compound AlkCH$_2$M [where Alk is an alkyl group such as n-propyl] with a compound $R^5R^6$CH$_2$ where necessary in the presence of a base such as an amine e.g. diisopropylamine using the above-mentioned conditions.

Intermediates of formula (5) where $L^2$ is a group —$X^a$H in which —$X^a$— is —NH— and $R^4$ is a hydrogen atom may be prepared from the known compound of formula (6)

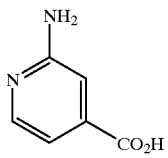
(6)

by reduction with a reducing agent, such as a lithium aluminium hydride, to give the alcohol derivative. This in turn may be oxidised, for example with manganese dioxide to afford an aldehyde of formula (5).

Intermediates of formula (3) where Z is a group (A) in which $R^3$ is a hydroxyl group may be prepared by reacting a ketone of formula (5) with a reagent $R^5$CHR$^6$R$^7$ using a base, such as an organometallic base, for example an organolithium reagent e.g. n-butyllithium, in a solvent, such as an ether, e.g. tetrahydrofuran, at around −70° C. to room temperature.

Ketones of formula (5) may be prepared by oxidation of an alcohol of formula (7)

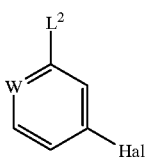
(7)

using an oxidising agent, such as manganese (IV) oxide, in a solvent, such as dichloromethane, at room temperature.

Alternatively, ketones of formula (5) may be prepared by reaction of a halide of formula (8)

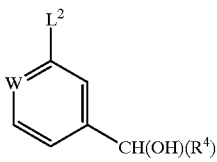
(8)

[where Hal is a halogen atom such as a bromine or chlorine atom] by halogen-metal exchange with a base such as n-butyllithium followed by reaction with a nitrile $R^4$CN, an acid chloride $R^4$COCl or an ester $R^4$CO$_2$A (where A is an alkyl group, e.g. a methyl group), in a solvent such as tetrahydrofuran at a low temperature, e.g. around −70° C., and subsequent treatment with an acid such as hydrochloric acid at e.g. −20° C. to ambient temperature.

Alcohols of formula (7) may be prepared
(1) by reacting a halide of formula (8) e.g. a bromide, with an aldehyde $R^4$CHO, in the presence of a base, such as n-butyllithium, in a solvent, e.g. tetrahydrofuran, at a temperature from around −70° C. to room temperature; or (2) by reacting an aldehyde of formula (9) where $W^a$ is a —CHO group (as described hereinbelow) with an organometallic compound, such as an organolithium $R^4$Li, or a Grignard $R^4$MgBr, in a solvent, such as tetrahydrofuran, at a low temperature, e.g. around −55° C. to 0° C.

Intermediates of formula (3) where Z is a group (B) may be prepared by condensing an intermediate of formula (9)

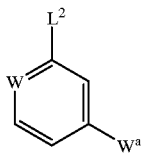
(9)

where
(a) $W^a$ is a —C(O)R$^4$ group wherein $R^4$ is as defined for formula (1) but is not a —CN or —CH$_2$CN group, with a compound $R^5$CH$_2$R$^6$; or where
(b) $W^a$ is a —CH$_2$R$^4$ group with an aldehyde or ketone $R^5$COR$^6$ where $R^5$ is as just defined for $R^4$; or where
(c) $W^a$ is a —C(O)R$^4$ group with a silane derivative (Alk$^a$)$_3$SiCH(R$^5$)(R$^6$), where Alk$^a$ is an alkyl group; in each instance in the presence of a base or an acid in a suitable solvent.

Bases for use in these reactions include inorganic bases, for example alkali and alkaline earth metal bases, e.g. hydroxides, such as sodium or potassium hydroxide; alkoxides, for example sodium ethoxide; organic bases, for example amines such as piperidine; and organolithium bases, such as alkyllithium, e.g. n-butyllithium bases. Suitable solvents include alcohols such as ethanol, or ethers such as tetrahydrofuran. Acids for use in the reactions include organic acids, e.g. carboxylic acids such as acetic acid.

The reactions may be performed at any suitable temperature, for example from around −78° C. to ambient temperature or to the reflux temperature depending on the nature of the starting materials.

In general, the base, acid, solvent and reaction conditions may be selected depending on the nature of the starting materials, from a range of known alternatives for reactions of this type.

In silane derivatives of formula (Alk$^a$)$_3$SiCH(R$^5$)(R$^6$), Alk$^a$ may be for example a C$_{1-6}$alkyl group such as a methyl group. Derivatives of this type may be prepared for example by reacting a compound $R^5$—CH$_2$—R$^6$ with a silane derivative, such as a chlorotrialkylsilane, e.g. chlorotrimethylsilane in the presence of a base, e.g. lithium diisopropylamide, in a solvent, e.g. tetrahydrofuran, at a low temperature, e.g. around −10° C.

The starting materials $R^5$COR$^6$ and $R^5$CH$_2$R$^6$ are either known compounds or may be prepared from known starting materials by methods analogous to those used for the preparation of the known compounds.

Intermediates of formula (9) where —$W^a$ is a —C(O)R$^4$ group where $R^4$ is an alkyl or aryl group (CH$_2$)$_r$Ar group, may be prepared by reacting an aldehyde of formula (9) where —$W^a$ is a —CHO group with an organometallic reagent in a solvent, e.g. tetrahydrofuran, at low temperature, e.g. around 10° C., followed by oxidation with an oxidising agent, such as manganese dioxide, in a solvent, e.g. dichloromethane.

Intermediates of formula (9) where —$W^a$ is —CHO may be prepared by reacting a compound of formula (8)

described above with an organometallic reagent, such as n-butyllithium, in a solvent, such as an amide, e.g. dimethylformamide, at a low temperature, e.g. below −60° C.

Intermediates of formula (8) may be prepared by deprotecting a compound of formula (10)

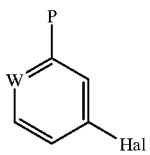

(10)

using reagents and conditions described herein for the obtention of an intermediate of formula (3) from an intermediate of formula (4) where $L^2$ is a group $X^aH$.

Intermediates of formula (10) may be prepared by protecting a compound of formula (11)

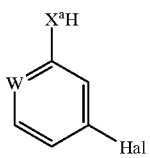

(11)

Examples of protecting groups include hydroxy, thio or amino protecting groups using conventional procedures [see Green, T. W. ibid]. Thus for example, where $X^a$ is an oxygen atom, the hydroxyl group may be protected as an ether group, using a reagent $Alk^bL^3$, where $Alk^b$ is an alkyl group and $L^3$ is a leaving group. Alkyl groups represented by $Alk^b$ include cycloalkyl groups, such as cyclopentyl group, and leaving groups $L^3$ include halogen atoms such as iodine, chlorine or bromine atoms or sulphonyloxy groups such as arylsulphonyloxy groups, e.g. p.toluenesulphonyloxy groups.

The reaction may be carried out in the presence of a base, e.g. an inorganic base such as a carbonate, e.g. caesium or potassium carbonate, an alkoxide, e.g. potassium-t-butoxide, or a hydride, e.g. sodium hydride, in a dipolar aprotic solvent such as an amide, e.g. a substituted amide such as dimethylformamide or an ether, e.g. a cyclic ether such as tetrahydrofuran, at ambient temperature or above. e.g. around 40° C. to 50° C.

Halides of formula (11) where $X^a$ is —O— may be prepared by oxydation of an aldehyde of formula (17) (where R is a hydrogen atom) as described below using an oxidising agent such as 3-chloroperoxybenzoic acid in a halogenated hydrocarbon such as chloroform at a temperature from around 0° C. to room temperature.

Halides of formula (11) where $X^a$ is —S— or —N($R^b$)— are either known compounds or may be prepared from known starting materials by methods analogous to those used for the preparation of the known compounds.

Compounds of formula (1) where Z is a group (A) in which $R^3$ is a hydroxyl group and $R^7$ is as described for compounds of formula (1) may be prepared by reacting a compound or formula (11) with a reagent $R^5R^6CHM$ or $R^5CHR^6R^7$ using the conditions described hereinabove for the obtention of an intermediate of formula (3) from a ketone of formula (5).

In another process according to the invention, compounds of formula (1) where Z is a group (B) and $R^4$ is a hydrogen atom or an alkyl or —$(CH_2)_rAr$ group may be prepared by reacting a compound of formula (12)

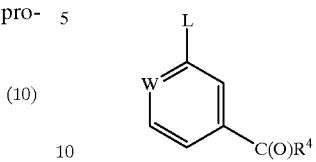

(12)

with a phosphonate ester $(R^dO)(OR^e)P(O)CH(R^5)(R^6)$ [where $R^d$ and $R^e$, which may be the same or different is an alkyl, or aralkyl group] in the presence of a base in a suitable solvent.

Suitable bases include organometallic bases such as organolithium, e.g. n-butyllithium, alkoxides, for example alkali metal alkoxides such as sodium ethoxide or sodium methoxide and a hydride such as potassium hydride or sodium hydride. Solvents include ethers, e.g. diethylether or cyclic ethers such as tetrahydrofuran and alcohol, e.g. methanol or ethanol.

The phosphonate derivatives used in this reaction are either known compounds or may be prepared by reacting a phosphite $P(OR^d)_2(OR^e)$ with a compound $R^5CHR^6Hal$ [where Hal is a halogen atom, for example a bromine atom] using conventional methods.

Intermediates of formula (12) where $R^4$ is a hydrogen atom may be prepared by reacting a halide of formula (13)

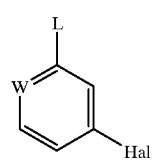

(13)

where Hal is a halogen atom, e.g. a bromine or chlorine atom with an organometallic reagent using the same reagents and conditions described above for the preparation of intermediates of formula (9) where $W^a$ is —CHO from intermediates of formula (8).

Intermediates of formula (2) where =W— is =N— and $R^4$ is H may be prepared from an acid of formula (14)

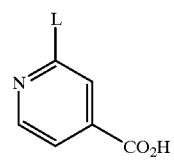

(14)

using the conditions described above for the preparation of an intermediate of formula (5) from an acid of formula (6).

Intermediates of formula (14) where L is $X^aAlk'Ar$ or $X^aR'$ and —$X^a$ is —O—, —S— or —NH—, may be prepared by reacting a halide of formula (15)

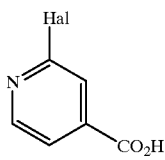

(15)

where Hal is a halogen atom, e.g. a bromine, chlorine or iodine atom with a compound ArAlk'X$^a$H, where —X$^a$— is —O—, —S— or —NH— in the presence of a base.

Bases used in this reaction include a hydride, such as sodium hydride, or an organometallic base such as butyl-lithium in a solvent, such as an amide, for example dimethylformamide at a temperature from room temperature to above, e.g. 80° C.

Intermediates of formula (15) may be prepared by reacting the known amine of formula (16)

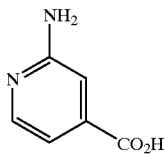

(16)

with nitrous acid (made in situ by reacting sodium nitrite with an acid, for example sulphuric acid or hydrobromic acid) to produce the diazonium salt. This in turn may be reacted with a haloacid, e.g. hydrobromic, hydrochloride or hydriodic acid if necessary in the presence of the corresponding copper (I), halide (CuBr or CuI) or halogen Br$_2$, Cl$_2$ or I$_2$.

Intermediates of formula (13) where L is a —C(R)=C(R$^1$)(R$^2$) group may be prepared by coupling a compound of formula (17)

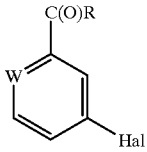

(17)

where Hal is a halogen atom, e.g. a bromine atom with a phosphonium salt (R$^1$)(R$^2$)CHP(D)$_3$Hal as described below for the preparation of compounds of formula (1) from intermediates of formula (19).

Intermediates of formula (12) where R$^4$ is an alkyl or —(CH$_2$)$_r$Ar group may be prepared by reaction of the corresponding compound of formula (12) where R$^4$ is a hydrogen atom with an organometallic reagent, followed by oxidation, as described previously for the preparation of intermediates of formula (9) where W$^a$ is —C(O)R$^4$ where R$^4$ is an alkyl or aryl group (CH$_2$)$_r$Ar from intermediates of formula (9) where R$^4$ is a hydrogen atom.

In another process for the preparation of compounds of formula (1) where Z is the group (B), an intermediate of formula (18)

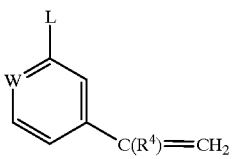

(18)

may be coupled in a Heck reaction with an organopalladium compound derived from a compound R$^5$Hal [where Hal is a halogen atom such as a bromine atom] and a palladium salt such as palladium acetate in the presence of a phosphine such as tri-o-tolylphosphine and a base such as triethylamine at an elevated temperature and pressure.

Intermediate alkenes of formula (18) may be obtained by reaction of a corresponding intermediate of formula (12) using a Wittig reaction employing a phosphonium salt such as methyltriphenylphosphonium bromide in the presence of a base such as n-butyllithium and an inert solvent such as tetrahydrofuran at, for example, 0° C. to ambient temperature.

Intermediates of formula (3) where L$^2$ is a —Alk'L$^3$ group in which Alk' is an alkenylene chain —C=C—Alk'— and L$^3$ is a hydroxyl group may be prepared by coupling a compound of formula (19)

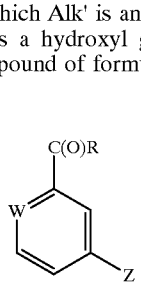

(19)

where R is a hydrogen atom or an alkyl group such as a methyl group, with an olefination agent.

Particular examples of olefination agents include phosphonium salts such as compounds HOAlk'P(D)$_3$Hal [where the hydroxyl group may need to be protected using conventional protecting group] where Hal is a halogen atom, such as a bromine atom and D is an optionally substituted alkyl, e.g. methyl, or aryl, especially phenyl group; phosphoranes HOAlk'C=P(D)$_3$; phosphonates (DO)$_2$P(O)Alk'OH; or silane derivatives, for example compounds of formula (D)$_3$SiAlk'OH e.g. trialkylsilanes such as (CH$_3$)$_3$SiAlk'OH.

Intermediates of formula (19) where R is an alkyl group, may be prepared by reacting an intermediate of formula (19) where R is a hydrogen atom with an organometallic reagent, such as an alkyllithium or an organomagnesium RMgHal, using the conditions described above, followed by oxidation of the resulting alcohol, using an oxidising agent, e.g. manganese dioxide.

Intermediates of formula (19) where R is a hydrogen atom may be prepared by deprotecting a protected aldehyde of formula (20)

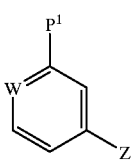

(20)

where P$^1$ is a protected aldehyde group, e.g. a dioxanyl group, using acid hydrolysis e.g. by reaction with trifluoroacetic acid or p-toluene sulphonic acid, in the presence of a solvent, e.g. acetone, or a mixture of solvents, e.g. chloroform and water.

Intermediates of formula (20) may be prepared by protecting an aldehyde or ketone of formula (19) with an aldehyde or ketone protecting group, using for example a suitable diol, e.g. 1,3-propanediol, in the presence of an acid catalyst, e.g. 4-toluene sulphonic acid, in a solvent, such as an aromatic solvent, e.g. toluene, at an elevated temperature.

In general, this reaction may be used when it is desired to protect an aldehyde in any intermediate described herein.

Compounds of formula (1) where L is a group —C(R)=C(R$^1$)(R$^2$) or Alk'Ar' where Alk' is an alkenylene chain —C=C—Alk' may be prepared from an intermediate of formula (19) using an appropriate olefination agent.

Particular examples of olefination agents include phosphonium salts such as compounds (R$^1$)(R$^2$)CHP(D)$_3$Hal or Ar'Alk'P(D)$_3$Hal where Hal is a halogen atom, such as a bromine atom, and D is an optionally substituted alkyl, e.g. methyl, or aryl, especially phenyl, group; phosphoranes (R$^1$)(R$^2$)C=P(D)$_3$ or Ar'Alk'=P(D)$_3$; phosphonates (DO)$_2$P(O)CH(R$^1$)(R$^2$) or (DO$_2$)P(O)Alk'Ar'; or silane derivatives, for example compounds of formula (D$_3$)SiC(R$^1$)(R$^2$) or (D$_3$)SiAlk'Ar', e.g. trialkylsilanes such as (CH$_3$)$_3$SiC(R$^1$)(R$^2$) or (CH$_3$)$_3$SiAlk'Ar'.

Bases for use in the above reaction include organometallic bases, for example, an organolithium compound such as an alkyllithium e.g. n-butyllithium, a hydride, such as sodium or potassium hydride or an alkoxide, such as a sodium alkoxide, e.g. sodium methoxide.

The reaction may be performed in a suitable solvent, for example a polar aprotic solvent, such as an alkyl sulphoxide, e.g. methyl sulphoxide, an amide such as N,N-dimethylformamide or hexamethylphosphorous triamide; a non-polar solvent, such as an ether, e.g. tetrahydrofuran or diethyl ether or an aromatic solvent such as benzene, toluene or xylene; or a polar protic solvent, such as an alcohol, for example ethanol. Preferably the reaction is carried out at a low temperature, for example from around −78° C. to around room temperature.

The olefination agents used in this reaction are either known compounds or may be prepared from known starting materials using reagents and conditions similar to those used to prepare the known compounds. For example, a phosphorane may be prepared in situ by reaction of a phosphonium salt with a base of the type described above. In another example, a phosphonate reagent may be prepared by reacting a halide Alk'Hal with a phosphite (DO)$_3$P, as described in the Arbuzov reaction. Silane derivatives may be prepared by reaction of a halosilane (D)$_3$SiHal where Hal is a halogen atom, for example a chlorine atom, with a base, such as lithium diisopropylamide, in a solvent, such as an ether, for example a cyclic ether, e.g. tetrahydrofuran, at low temperature, e.g. −10° C.

According to a further aspect of the invention, compounds of formula (1) where L is a group —C(R)=CH(R$^1$) and R$^1$ is an optionally substituted alkyl, alkenyl or alkenyl group may also be prepared by reaction of an intermediate of formula (19) with an organometallic reagent, followed by dehydration of the corresponding alcohol.

Examples of organometallic reagents include organolithium R$^1$Li or organomagnesium R$^1$MgHal reagents. The reaction with the organometallic reagent may be performed in a solvent such as an ether, e.g. diethyl ether or for example a cyclic ether such as tetrahydrofuran, at a low temperature for example −10° C. to room temperature. The dehydration may be performed using an acid, for example an organic acid such as p.toluene sulphonic acid or trifluoracetic acid, in the presence of a base, such as an amine, e.g. triethylamine.

In yet another process according to the invention, compounds of formula (1) wherein R$^3$, R$^6$ and R$^7$ is each a hydrogen atom may be prepared by decarboxylation of an acid of formula (21):

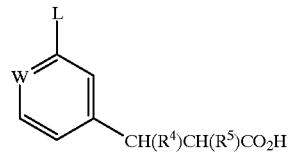

(21)

The reaction may be carried out by treatment of the compound of formula (21) with a base, for example an inorganic base such as a hydroxide, e.g. sodium hydroxide in a solvent such as an alcohol, e.g. ethanol, at an elevated temperature e.g. the reflux temperature, followed by acidification of the reaction mixture to a pH of around pH4 to around pH6 using an acid such as an inorganic acid, e.g. hydrochloric acid, at an elevated temperature, e.g. the reflux temperature.

If desired, the acid of formula (21) may be generated in situ from the corresponding ester or nitrile using the above reaction conditions, or by initial treatment with an acid.

Intermediates of formula (21) may be prepared by reacting a compound of formula (22)

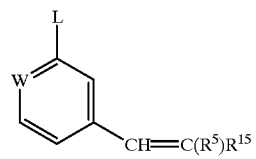

(22)

[where R$^{15}$ is an ester of an acid —CO$_2$H (e.g. an alkyl ester such as an ethyl ester) or a nitrile —CN], with a Grignard reagent R$^4$MgBr, in the presence of a complexing agent, e.g. a copper (I) bromide-dimethyl sulphide complex, or a copper (I) chloride, or with an organolithium compound, e.g. R$^4$Li, in a solvent, e.g. tetrahydrofuran, at low temperature, e.g. around −40° C., followed by treatment with a base or an acid to yield the acid of formula (21). The Grignard and the lithium reagents are either known compounds or may be prepared in a manner similar to that used to synthesise the known compounds.

Compounds of formula (22) may be obtained by reacting an adehyde of formula (12) with an ester or nitrile R$^5$CH$_2$R$^{15}$ in an acid solvent, such as acetic acid, at an elevated temperature, for example the reflux temperature, in the presence of a base, such as ammonium acetate.

In a further process according to the invention a compound of formula (1) wherein R$^3$, R$^6$ and R$^7$ is each a hydrogen atom and R$^5$ is a heteroaryl group may be generally prepared by cyclisation of a compound of formula (23):

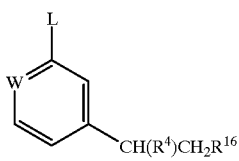

(23)

where $R^{16}$ is a carboxylic acid [—$CO_2H$] group or a reactive derivative thereof; or a nitrile [—CN] or an imine salt with a bifunctional reagent $W^1R^{5a}W_2$ and, where necessary, a compound $R^{5b}W^3$ [where $W^1$, $W^2$ and $W^3$, which may be the same or different, is each a reactive functional group or a protected derivative thereof; and $R^{5a}$ and $R^{5b}$ are components of the heteroaryl group $R^5$ such that when added together with $W^1$, $W^2$ and $W^3$ to the group $R^{16}$ in compounds of formula (23) the resulting group —$RW^1R^{5a}W^2$ or —$RW^1R^{5a}W^2R^{5b}W^3$ constitutes the heteroaryl group $R^5$].

Reactive derivatives of carboxylic acids for use in this reaction include acid halides, (e.g. acid chlorides), amides, including thioamides, or esters, including thioesters. Imine salts include for example salts of formula [e.g. —C(OAlk)=$NH_2^+A^-$, where Alk is a $C_{1-4}$alkyl group and $A^-$ is a counterion e.g. a chloride ion].

In this general reaction the reactive functional groups represented by $W^1$, $W^2$ or $W^3$ may be any suitable carbon, nitrogen, sulphur or oxygen nucleophiles. Particular examples include simple nucleophiles such as carbanions [e.g. generated by the coupling of an alkyl group with an organometallic compound], amino, thiol and hydroxyl groups.

In general, the cyclisation reaction will initially be performed in a solvent, for example an inert solvent such as a halocarbon, e.g. dichloromethane, an ether, e.g. a cyclic ether such as tetrahydrofuran, or a hydrocarbon, e.g. an aromatic hydrocarbon such as toluene, from a low temperature, e.g. around −70° C., to around the reflux temperature, where necessary in the presence of a base or a thiation reagent, e.g. Lawesson's reagent, followed if necessary by heating, to an elevated temperature, e.g. the reflux temperature.

Thus, in one particular example, compounds of formula (1) wherein $R^3$, $R^6$ and $R^7$ is each a hydrogen atom and $R^5$ is a benzothiazolyl, benzoxazolyl or benzimidazolyl group may be prepared by reaction of a compound of formula (19) where $R^{16}$ is an acid halide, e.g. acid chloride, with a reagent $W^1R^{5a}W^2$ which is 2-aminothiophenol, 2-hydroxyphenol, or 1,2-diaminobenzene respectively in the presence of a base e.g. an organic amine such as pyridine, in a solvent e.g. a halocarbon such as dichloromethane, from around −70° C. to the reflux temperature.

In another example of the general cyclisation process, a compound of formula (23) where $R^{16}$ is an acid halide as described above may be reacted with a compound $W^1R^{5a}W^2$ which is a monoalkylmalonate, e.g. ethyl hydrogen malonate, followed by reaction with a compound $R^{5b}W^3$ which is hydrazine to give a compound of formula (1) wherein $R^3$, $R^6$ and $R^7$ is each a hydrogen atom and $R^5$ is a 5-hydroxypyrazolyl group.

In another variation of the cyclisation process, the halide of formula (23) may be reacted with a compound $W^1R^{5a}W^2$ which is $BrMg(CH_2)_3[$—$O(CH_2)_2O$—$]$ followed by reaction in an acid solution with a compound $R^{5b}W^3$ which is methylamine to yield a compound of formula (1) wherein $R^3$, $R^6$ and $R^7$ is each a hydrogen atom and $R^5$ is a N-methyl pyrrole group.

In a further example of the cyclisation process, the acid halide of formula (23) may be reacted with a compound $W^1R^{5a}W^2$ which is $H_2NNHCSNH_2$ in an aromatic hydrocarbon such as toluene, at an elevated temperature, e.g. around 150° C., followed by treatment with a base, e.g. an inorganic base such as sodium bicarbonate to give a compound of formula (1) wherein $R^3$, $R^6$ and $R^7$ is each a hydrogen atom and $R^5$ is a 1,2,4-triazolyl-5-thiolate group.

Intermediate compounds of formula (23) are particularly useful and form a further aspect of the invention. Active derivatives of the acids of formula (23) and other compounds of formula (23) where $R^{16}$ is a nitrile or an imine salt may be prepared from the corresponding acids [where $R^{16}$ is —$CO_2H$] using conventional procedures for converting carboxylic acids to such compounds, for example as described in the Examples hereinafter.

Acids of formula (23) [where $R^{16}$ is —$CO_2H$] may be prepared by hydrolysing a diester of formula (24)

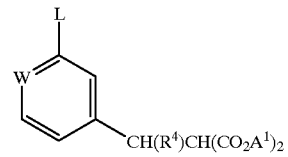

(24)

where $A^1$ is a $C_{1-4}$alkyl group, e.g. an ethyl group, with a base, e.g. sodium hydroxide, in a solvent, e.g. dioxane, at an elevated temperature, e.g. the reflux temperature, followed by acidification at an elevated temperature.

Diesters of formula (24) may be prepared by reacting a diester of formula (24)

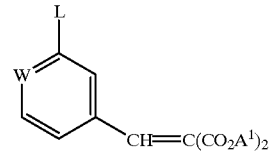

(24)

with an organometallic reagent, such as a Grignard reagent using the conditions described above for the preparation of alcohols of formula (1).

In yet another process according to the invention, a compound of formula (1) where Z is a group (C) may be prepared by coupling a compound of formula (25),

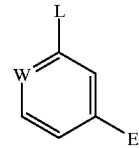

(25)

where E is a boronic acid —$B(OH)_2$ or a tin reagent $Sn(R)_3$, in which R is an alkyl group, for example a methyl group, with a reagent Z—$L^4$, where $L^4$ is a leaving group, in the presence of a complex metal catalyst.

Particular leaving groups $L^4$ include for example halogen atoms, e.g. bromine, iodine or chlorine atoms and an alkyl sulphonate, such as trifluoromethanesulphonate.

Suitable catalysts include heavy metal catalysts, for example palladium catalysts, such as tetrakis (triphenylphosphine)palladium. The reaction may be performed in an inert solvent, for example an aromatic hydrocarbon such as toluene or benzene, or an ether, such as dimethoxyethane or dioxane, if necessary in the presence of a base, e.g. an alkali carbonate such as sodium carbonate, at an elevated temperature, e.g. the reflux temperature. In general, the metal catalyst and reaction conditions may be selected, depending on the nature of the compound of formula (25) and/or the compound Z—$L^4$ from a range of known alternatives for reactions of this type [see for example Miyaura, N et al, Synth. Comm. (1981), 11, 513; Thompson, W. J. and Gaudino, J., J. Org. Chem, (1984), 49, 5237 and Sharp, M. J. et al, Tetrahedron Lett. (1987), 28, 5093].

Intermediates Z—$L^4$ are either known compounds or may be prepared from known starting materials by methods analogous to those used for the preparation of the known compounds. Thus, for example, where it is desired to obtain a compound Z—$L^4$ where $L^4$ is a halogen atom such as bromine or chlorine atom and this compound is not readily available, such a compound may be prepared by (1) treatment of the corresponding amine with t-butyl nitrite and anhydrous $CuCl_2$ or $CuBr_2$ at elevated temperature, or (2) with t-butyl thionitrite or t-butyl thionitrate and $CuCl_2$ or $CuBr_2$ at room temperature followed by reaction with an appropriate copper (I) halide such as cuprous chloride or bromide in an aqueous acid.

Intermediates of formula (25) may be prepared by halogen-metal exchange between a compound of formula (13) where Hal is a bromine atom and an organometallic agent such as n-butyl or t-butyllithium followed by reaction with a borate such as triisopropylborate or a tin reagent $(R)_3SnX$, where R is as described above and X is a halogen atom, such as chlorine atom, optionally at a low temperature e.g. around −70° C., in a solvent such as tetrahydrofuran.

According to another aspect of the invention, a compound of formula (1) where Z is a group (D) in which —$Z^1$ is —$NR^{12}C(O)$— or —$C(O)NR^{12}$— may be prepared by coupling a compound of formula (26)

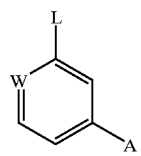

(26)

where —A is a —$CO_2H$ or —$NHR^{12}$ group,
or an active derivative thereof with a compound $R^{12}NH(Alk)_t(X)_nAr$ or $Ar(X)_n(Alk)_tCO_2H$ or an active derivative thereof. Active derivatives of acids of formula (26) or $Ar(X)_n(Alk)_tCO_2H$ include, for example, acid anhydrides, or acid halides, such as acid chlorides.

The coupling reaction may be performed using standard conditions for reactions of this type. Thus for example, the reaction may be carried out in a solvent, for example an inert organic solvent such as an ether, e.g. a cyclic ether such as tetrahydrofuran, an amide, e.g. a substituted amide such as dimethylformamide, or a halogenated hydrocarbon such as dichloromethane, at a low temperature, e.g. −30° C. to ambient temperature such as −20° C. to 0° C., optionally in the presence of a base, e.g. an organic base such as an amine, e.g. triethylamine or a cyclic amine such as N-methylmorpholine. Where an acid of formula (17) or $Ar(X)_n(Alk)_tCO_2H$ is used, the reaction may additionally be performed in the presence of a condensing agent, for example a diimide such as N,N'-dicyclohexylcarbodiimide, advantageously in the presence of a triazole such as 1-hydroxybenzotriazole. Alternatively, the acid may be reacted with a chloroformate, for example ethylchloroformate, prior to reaction with the amine.

Intermediate acids of formula (26) where A is a —$CO_2H$ group may be prepared by hydrolysis of a corresponding ester of formula (27)

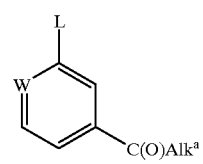

(27)

where $Alk^a$ is an alkyl group;
by heating in the presence of a base, for example an alkali metal hydroxide such as lithium hydroxide in a solvent such as an alcohol, e.g. methanol.

Intermediates of formula (26) where A is a —$NHR^{12}$ group and $R^{12}$ is a hydrogen atom, may be prepared by hydrogenation of a corresponding nitro compound of formula (28)

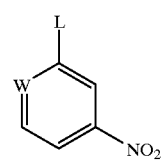

(28)

using the reagents described below for the hydrogenation of a compound of formula (1) where —L is a —$CH=C(R^1)(R^2)$ chain to a compound of formula (1) where —L is a —$CH_2CH(R^1)(R^2)$ chain.

Intermediates of formula (26) where A is a $NHR^{12}$ group in which $R^{12}$ is an alkyl group may be prepared by alkylation of an intermediate of formula (26) in which $R^{12}$ is a hydrogen atom, using an alkyl halide e.g. an alkyl iodide in a solvent, such as an aromatic solvent, for example benzene.

Intermediates of formulae (27) and (28) and the reagents $R^{12}NH(Alk)_t(X)_nAr$ and $Ar(X)_n(Alk)_tCO_2H$ are known compounds or may be prepared from known starting materials by methods analogous to those used for the preparation of the known compounds.

In yet another aspect of the invention compounds of formula (1) where Z is a group(D) in which $Z^1$ is a —$C\equiv C$— chain and n and t is each zero may be prepared by reacting a compound of formula (29)

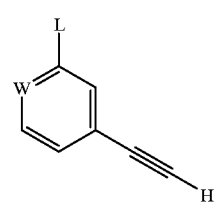

(29)

with a reagent $Ar(X)_n(Alk)_tL^5$ (where $L^5$ is a leaving group) in the presence of a metal complex catalyst, and in a solvent Examples of $L^5$ leaving groups include halogen atoms such as bromine, iodine or chlorine atoms or alkyl triflate such as trifluoromethane sulphonate. Suitable solvents include for example an amine, for example a tertiary amine, e.g. triethylamine, a secondary amine, e.g. dimethylamine or a primary amine e.g. n-butylamine.

Metal complex catalysts include palladium catalysts, such as Pd(Hal)$_2$(PPh$_3$)$_2$ or Pd(PPh$_3$)$_4$ (where Hal is a halogen atom e.g. a chlorine atom) in the presence of copper (I) iodide, at a temperature from room temperature to an elevated temperature, e.g. the reflux temperature. (Comprehensive organic synthesis, vol. 3., 531–541; Trost, Fleming. Pergamon Press, 1991).

Intermediates of formula (29) may be prepared by reacting a dihalide of formula (30)

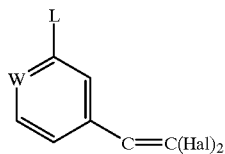

(30)

where Hal is a halogen atom, e.g. a bromine atom, with a base such as an organometallic base, for example an organolithium, e.g. n-butyllithium, in a solvent such as an ether, e.g. tetrahydrofuran or diethylether, at a temperature from around –78° C. to room temperature.

Intermediates of formula (30) may be prepared by reacting an aldehyde of formula (12) (where R$^4$ is a hydrogen atom) with a reagent Hal$_2$C=P(Ar$^1$)$_3$ (where Hal is a halogen atom, such as a bromine atom and Ar$^1$ is an aryl group, such as phenyl or o-tolyl), prepared in situ from C(Hal)$_4$ and P(Ar$^1$)$_3$ in the presence of a base, such a an organometallic base, for example an organolithium, e.g. n-butyllithium).

In a futher aspect of the invention, compounds of formula (1) where Z is a group (D) in which Z$^1$ is a —NR$^{12}$SO$_2$— or —SO$_2$NR$^{12}$— group may be prepared by reaction of a compound of formula (30)

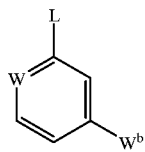

(30)

where (a) W$^b$ is a —NHR$^{12}$ group with a compound Ar(X)$_n$(Alk)$_t$SO$_2$Hal [where Hal is a halogen atom, e.g. a bromine or chlorine atom], if necessary in the presence of a base; or, (b) W$^b$ is a —SO$_2$Hal group with a compound Ar(X)$_n$(Alk)$_t$NHR$^{12}$ using the reagents and conditions described in (a) above.

Examples of bases used in this reaction include amine, such as tertiary amine, for example triethylamine, in a solvent such as an ether, for example a cyclic ether, e.g. tetrahydrofuran. Compounds Ar (X)$_n$(Alk)$_t$NHR$^{12}$ and compounds of formula (30) where W$^b$ is a —NHR$^{12}$ group are known compounds or may be prepared using similar reagents and conditions to those used to prepare the known compounds.

Compounds of formula (30) where W$^b$ is —SO$_2$Hal, may be prepared by reacting an intermediate halide of formula (13) with an organometallic reagent, such as an organolithium, e.g. n-butyllithium in a solvent, such as an ether, e.g. tetrahydrofuran, at a low temperature e.g. around –60° C. to –100° C. followed by reaction with sulphuryl chloride, in a solvent, such as an aliphatic solvent, e.g. n-hexane, at a low temperature, e.g. around 0° C.

Compounds of formula (1) where L is a group —CH(R$^1$)(R$^2$) where R$^2$ is a —CO$_2$H group may be prepared by reacting a compound of formula (31)

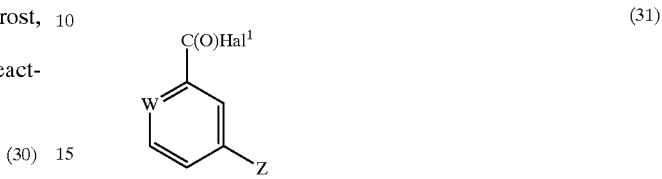

(31)

where Hal$^1$ is a halogen atom, such as a chlorine or a bromine atom, with a diazoalkane CH(R$^1$)N$_2$ to give the corresponding diazoketone derivative which is then treated with water and silver oxide or with silver benzoate and triethylamine.

Intermediates of formula (31) may be prepared by oxidation of an aldehyde of formula (19), using an oxidising agent, such as permanganate or chromic acid, to give the corresponding carboxylic acid which is then reacted with a halide reagent, such as thionylchloride, phosphorous pentachloride or phosphorous pentabromide.

Compounds of formula (1) may also be prepared by interconverting other compounds of formula (1). Thus, for example where Z is a group (A) in which R$^3$ is a hydrogen atom may be prepared by hydrogenation of a compound of formula (1) where Z is a group (B).

The hydrogenation may be performed using for example hydrogen in the presence of a catalyst. Suitable catalysts include metals such as platinum or palladium optionally supported on an inert carrier such as carbon or calcium carbonate; nickel, e.g. Raney nickel, or rhodium. The reaction may be performed in a suitable solvent, for example an alcohol such as methanol or ethanol, an ether such as tetrahydrofuran or dioxane, or an ester such as ethyl acetate, optionally in the presence of a base, for example a tertiary organic base such as triethylamine, at for example ambient temperature.

Alternatively, the reaction may be accomplished by transfer hydrogenation using an organic hydrogen donor and a transfer agent. Suitable hydrogen donors include for example acids, such as formic acid, formates, e.g. ammonium formate, alcohols, such as benzyl alcohol or ethylene glycol, hydrazine, and cycloalkenes such as cyclohexene or cyclohexadiene. The transfer agent may be for example a transition metal, for example palladium or platinum, optionally supported on an inert carrier as discussed above, nickel, e.g. Raney nickel, ruthenium, e.g. tris (triphenylphosphine) ruthenium chloride or copper. The reaction may generally be performed at an ambient or elevated temperature, optionally in the presence of a solvent, for example an alcohol such as ethanol or an acid such as acetic acid.

In a second example of an interconversion process, compounds of formula (1) where Z is a group (A) in which R$^7$ is an OR$^c$ group where R$^c$ is an alkyl or alkenyl group, may be prepared by reacting a compound of formula (1) where Z is a group (A) in which R$^7$ is a —OH group, with a reagent R$^c$—OH, in the presence of an acid, such as sulphuric acid.

In another example of an interconversion process, compounds of formula (1) where Z is a group (A) in which R$^7$ is an OR$^c$ group where R$^c$ is a carboxamido or thiocarboxamido group may be prepared by reaction of a compound of formula (1) where Z is a group (A) in which $R^7$ is a —OH group, with an isocyanate $R^cN=C=O$ or an isothiocyanate $R^cN=C=S$ in the presence of a base, such as sodium hydride, in a solvent, such as tetrahydrofuran. Compounds $R^cN=C=O$ and $R^cN=C=S$ are known compounds or may be prepared using the reagents and conditions used for the preparation of the known compounds. When $R^cN=C=S$ is not available, a compound of formula (1) where $R^c$ is a thiocarboxamido group may be prepared by interconverting a compound of formula (1) where $R^c$ is a carboxamido group using a thiation reagent, such as Lawesson's reagent [2,4-bis(4-methoxyphenyl)-1,3,2,4-dithiadiphosphetane-2,4-di-sulphide], in an aromatic solvent, such as xylene or toluene.

In a yet another example of an interconversion process, a compound of formula (1) where Z is a group (A) in which $R^3$ is a fluorine atom may be prepared by reacting a compound of formula (1) where Z is a group (A) in which $R^3$ is a hydroxyl group, with a fluorinating reagent, such as diethylaminosulphur trifluoride (DAST), in a solvent, for example a chlorinated solvent, e.g. dichloromethane, at a low temperature, e.g. around 0° C.

In a still further example of an interconversion process, a compound of formula (1) where Z is a group (A) in which $R^3$ is an alkyl group, may be prepared by alkylation of a compound of formula (1) where Z is a group (A), and $R^3$ is a hydrogen atom, with a reagent $R^3L^3$ using a base, for example n-butyllithium or lithium diisopropylamide. In this process, $R^4$ in the starting material is preferably an electron withdrawing group.

In a still further example of interconversion process, a compound of formula (1) where L is $(X^a)_nAlk'Ar'$ or $Alk'X^aAr'$ where Alk' is an alkylene chain, may be prepared by hydrogenation of a compound of formula (1) where Alk' is an alkenylene or alkynylene chain, using for example hydrogen in the presence of a metal catalyst, as described above for the hydrogenation of a compound of formula (1) where Z is a group (B) to give a compound of formula (1) where Z is the group A.

Compounds of formula (1) where Z is the group (B) may also be prepared by dehydrating a compound of formula (1) where Z is the group (A) and $R^3$ is a hydroxyl group, by using an acid, e.g. trifluoroacetic acid, in the presence of a base, such as an amine, e.g. triethylamine, in a solvent, such as dichloromethane, at a low temperature, e.g. around −10° C.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral acid or base. Suitable chiral acids include, for example, tartaric acid and other tartrates such as dibenzoyl tartrates and ditoluoyl tartrates, sulphonates such as camphor sulphonates, mandelic acid and other mandelates and phosphates such as 1,1'-binaphthalene-2,2-diyl hydrogen phosphate. The diastereomers may then be separated by any convenient means, for example by crystallisation and the desired enantiomer recovered, e.g. by treatment with an acid or base in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate acid or base in a suitable solvent or mixture of solvents e.g. an organic solvent such as an ether e.g. diethylether, or an alcohol, e.g. ethanol using conventional procedures.

The following Examples illustrate the invention. In the Examples, the following abbreviations are used DME—ethylene glycol dimethyl ether; THF—tetrahydrofuran; $CH_2Cl_2$—dichloromethane; $Et_2O$—ether; EtOH—ethanol; RT—room temperature; DMF—N,N-dimethylformamide; EtOAc—ethyl acetate; MeOH—methanol.

Intermediates 1–6 were prepared as described in International Patent Specification No. WO 94/14742.

INTERMEDIATE 1

3-Cyclopentyloxy-4-methoxybenzaldehyde

INTERMEDIATE 2

(3-Cyclopentyloxy-4-methoxyphenyl)phenylketone

INTERMEDIATE 3

(±)-4-[2-(3-Cyclopentyloxy-4-methoxyphenyl)-2-hydroxy-2-phenylethyl]pyridine

INTERMEDIATE 4

(E) and (Z) isomers of 4-[2-(3-Cyclopentyloxy-4-methoxyphenyl)-2-phenylethenyl]pyridine

INTERMEDIATE 5

(±)-4-[2-(3-Cyclopentyloxy-4-methoxyphenyl)-2-phenylethyl]pyridine

INTERMEDIATE 6

(i) (+)-4-[2-(3-Cyclopentyloxy-4-methoxyphenyl)-2-phenylethyl]pyridine (ii) (−)-4-[2-(3-Cyclopentyloxy-4-methoxyphenyl)-2-phenylethyl]pyridine

INTERMEDIATE 7 a) (R)-4-[2-(3-Hydroxy-4-methoxyphenyl)-2-phenylethyl]pyridine

Intermediate 6 (i) (430 mg) in dioxane/water (20 ml:10 ml) containing concentrated $H_2SO_4$ (10 ml) was heated at 90° C. for 1 h. The reaction mixture was cooled, neutralised with aqueous $NaHCO_3$ then concentrated in vacuo. The residue was partitioned between EtOAc (25 ml) and $H_2O$ (15 ml), and the organic phase separated. The extract was washed with brine (25 ml), dried ($MgSO_4$) and concentrated in vacuo. The residue was recrystallised (EtOH) to afford the title compound (240 mg) as an off-white crystalline solid m.p. 195–197° C. (Found: C, 78.66; H, 627; N, 4.59. $C_{20}H_{19}NO_2$ requires C, 78.64; H, 6.18; N, 4.42%); δH (CDCl$_3$) 3.30 (2H, d, J 8 Hz, CHC$\underline{H}_2$), 3.86 (3H, s, O$\underline{Me}$), 4.13 (1H, t, J 8 Hz, C$\underline{H}$CH$_2$), 5.7 (1H, br s, O$\underline{H}$), 6.63 (1H, dd, J 8.3 Hz, Ar$\underline{H}$ para to OH), 6.71 (1H, d, J 8.3 Hz, Ar$\underline{H}$ ortho to OMe), 6.80 (1H, d, J 2.2 Hz, Ar$\underline{H}$ ortho to OH), 6.93 (2H, dd, J 4.5, 1.5 Hz, pyridine $\underline{H}_3$, $\underline{H}_5$), 7.1–7.3 (5H, m, $C_6H_5$), and 8.37 (2H, dd, J 4.5, 1.5 Hz, pyridine $\underline{H}_2,\underline{H}_6$).

The following Intermediate was prepared in a manner similar to Intermediate 7a)

b) (E)-4-[2-(3-Hydroxy-4-methoxyphenyl)ethenyl]pyridine

From Intermediate 20 (8.0 g, 27.1 mmol) in toluene (200 ml) and p-toluenesulphonic acid $H_2O$ (10.3 g, 54.2 mmol) under a nitrogen atmosphere. Recrystallisation (EtOH) gave the title compound (3.8 g) as an amorphous yellow solid. m.p. 196–199° C. (Found C, 73.73; H, 6.03; N, 6.06. $C_{14}H_{13}NO_2$ requires C, 73.99; H, 5.77; N, 6.16%). δH (300 MHz; CDCl$_3$) 3.92 (3H, s, OC$\underline{H}_3$), 6.22 (1H, br s, O$\underline{H}$), 6.86 (1H, d, $\underline{H}$ 8.3 Hz, Ar$\underline{H}_4$), 6.86 (1H, d, J 16.2 Hz, $\underline{H}$C═C (trans)), 7.01 (1H, dd, J 8.3, 2.1 Hz, Ar$\underline{H}_6$), 7.17–7.26 (2H, m, Ar$\underline{H}_2$ and $\underline{H}$C═C), 7.34 (2H, dd, J 4.6, 1.6 Hz, pyridine $\underline{H}_3$, $\underline{H}_5$), and 8.55 (2H, t, J 4.6, 1.4 Hz, pyridine $\underline{H}_2,\underline{H}_6$).

INTERMEDIATE 8

2-Methoxy-4-(3-pyridyl)benzaldehyde

A mixture of 5-bromo-2-methoxybenzaldehyde (10.00 g, 1.82 mmol) and tetrakis (triphenylphosphine)palladium (O) (2.10 g, 1.82 mmol, 3.9 mol %) in DME (filtered through $Al_2O_3$) (50 ml) was stirred at RT for 0.25 h. Sodium carbonate (2M, 50 ml, 0.10 mol %) and diethyl (3-pyridyl)borane (6.817 g, 46.36 mmol) were added, the mixture heated to reflux for 5.5 h then allowed to stand at RT overnight. The dark brown reaction mixture was partitioned between water (50 ml) and Et$_2$O (100 ml) and the organic layer separated and combined with two further Et$_2$O extracts (1×50 ml, 1×25 ml). The organic phase was extracted with 2N hydrochloric acid (2×50 ml) then the aqueous extract was basified with 3M NaOH and extracted with Et$_2$O (1×150 ml, 2×50 ml). The combined organic extract was washed with brine (50 ml), dried (Na$_2$SO$_4$), concentrated in vacuo then submitted to column chromatography [SiO$_2$; Et$_2$O] to furnish the title compound (3.318 g) as a pale yellow solid (Found: C, 73.40; H, 5.20; N, 6.44. $C_{13}H_{11}NO_2$ requires C, 73.23; H, 5.20; N, 6.57%.).

INTERMEDIATE 9

2-(5-Bromo-2-methoxyphenyl)-1,3-dioxane

A mixture of 5-bromo-2-methoxybenzaldehyde (52.3 g, 243 mmol), 1,3-propanediol (30 ml, 31.6 g, 415 mmol), and 4-toluenesulphonic acid (0.3 g) in toluene (350 ml) was heated to reflux in a Dean-Stark apparatus for 20 h. The mixture was cooled to RT, washed with saturated NaHCO$_3$ solution (100 ml), then the organic layer was separated and combined with a CH$_2$Cl$_2$ solution (100 ml). The extract was washed (brine; 50 ml), dried (Na$_2$SO$_4$), and concentrated in vacuo to give a brown oil (66.2 g). The crude product was distilled to afford the title compound (58.2 g) as a colourless viscous oil b.p. 115–120° C., 0.02 mmHg δH (80 MHz; CDCl$_3$) 1.2–1.5 (1H, br m, CH$_2$C$\underline{H}$HCH$_2$), 1.9–2.4 (1H, m, CH$_2$CH$\underline{H}$CH$_2$), 3.78 (3H, s, O$\underline{Me}$), 3.6–4.4 (4H, m, C$\underline{H}_2$CH$_2$C$\underline{H}_2$), 5.76 (1H, s, OC$\underline{H}$), 6.67 (1H, d, J 8.8 Hz, Ar$\underline{H}$ ortho to OMe), 7.33 (1H, dd, J 8.8, 2.3 Hz, Ar$\underline{H}$ para to acetal), and 7.68 (1H, d, J 2.3 Hz, Ar$\underline{H}$ ortho to acetal); m/z (El) 274 (44%), 273 (31), 272 (45), 271 (27), 216 (34), 215 (47), 214 (35), 213 (44), 193 (34), 135 (22), and 87 (100).

INTERMEDIATE 10

3-[2-(1,3-Dioxanyl)]-4-methoxybenzaldehyde n-BuLi (1,6$\underline{M}$ solution in hexane) (125 ml, 200 mmol, 1.06 equiv.) was added dropwise to a solution of Intermediate 9 (51.65 g, 189 mmol) in THF (250 ml) at below −65° C. After 3.5 h, DMF (20 ml, 258 mmol, 1.37 equiv.) was added at below −60° C. The reaction mixture was allowed to warm to RT then poured into hydrochloric acid (0.05 $\underline{M}$; 500 ml) and immediately extracted with CH$_2$Cl$_2$ (500 ml, 2×150 ml). The extract was washed (brine; 200 ml), dried (K$_2$CO$_3$), and concentrated in vacuo to give a pale yellow oil (44.0 g). The crude product was triturated with warm hexane (250 ml) to afford the title compound (38.75 g) as an off-white crystalline solid δH (80 MHz; CDCl$_3$) 1.3–1.6 (1H, br m, CH$_2$C$\underline{H}$HCH$_2$), 1.8–2.5 (1H, m, CH$_2$CH$\underline{H}$CH$_2$), 3.89 (3H, s, O$\underline{Me}$), 3.7–4.4 (4H, m, C$\underline{H}_2$CH$_2$C$\underline{H}_2$), 5.82 (1H, s, OC$\underline{H}$), 6.93 (1H, d, J 8.4 Hz, Ar$\underline{H}$ ortho to OMe), 7.82 (1H, dd, J 8.4, 2.2 Hz, Ar$\underline{H}$ para to acetal), 8.12 (1H, d, J 2.2 Hz, Ar$\underline{H}$ ortho to acetal), and 9.84 (1H, s, C$\underline{H}$O).

INTERMEDIATE 11

3-[3-(1,3-Dioxan-2-yl)-4-methoxyphenyl]-2-(4-pyridyl)propenenitrile

A mixture of Intermediate 10 (15.0 g, 67.5 mmol) and 4-pyridylacetonitrile hydrochloride (10.75 g, 69.5 mmol) was stirred at RT in a mixture of EtOH (300 ml) and NaOH solution (3$\underline{M}$; 40 ml, 150 mmol). After 1 h, the precipitate was collected by filtration, washed with EtOH (50 ml), then Et$_2$O (25 ml) and dried in vacuo to afford the title compound (15.85 g) as a very pale yellow solid δH (80 MHz; CDCl$_3$) 1.3–1.7 (1H, br m, CH$_2$C$\underline{H}$HCH$_2$), 2.0–2.4 (1H, m, CH$_2$CH$\underline{H}$CH$_2$), 3.90 (3H, s, O$\underline{Me}$), 3.8–4.4 (4H, m, C$\underline{H}_2$CH$_2$C$\underline{H}_2$), 5.83 (1H, s, OC$\underline{H}$), 6.95 (1H, d, J 8.5 Hz, Ar$\underline{H}$ ortho to OMe), 7.47 (2H, dd, J 4.6, 1.7 Hz, pyridine $\underline{H}_3$, $\underline{H}_5$), 7.63 (1H, s, C$\underline{H}$═C), 7.96 (1H, d, J 2.4 Hz, Ar$\underline{H}$ ortho to acetal), 8.20 (1H, dd, J 8.5, 2.4 Hz, Ar$\underline{H}$ para to acetal), and 8.61 (2H, dd, J 4.6, 1.7 Hz, pyridine $\underline{H}_2$, $\underline{H}_6$).

INTERMEDIATE 12

5-Bromo-2-methoxybenzylidenecyclopentane n-BuLi (1.6$\underline{M}$ solution in hexane) (72.5 ml, 116 mmol) was added dropwise at 0° C. to a solution of cyclopentyltriphenylphosphonium bromide (45.8 g, 111 mmol) in THF (300 ml). The red solution was stirred at 0° C. for 0.5 h then treated with a solution of 5-bromo-2-methoxybenzaldehyde (23.5 g, 109 mmol) in THF (150 ml). The reaction mixture was stirred at RT overnight, concentrated in vacuo, then partitioned between CH$_2$Cl$_2$ (250 ml) and water (150 ml). The organic phase was separated and combined with further CH$_2$Cl$_2$ extracts (2×50 ml). The organic phase was washed (brine; 50 ml), dried (Na$_2$SO$_4$), and concentrated in vacuo. The residue was subjected to chromatography (SiO$_2$; CH$_2$Cl$_2$) to afford the title compound (24.6 g), as a colourless oil δH (80 MHz; CDCl$_3$) 1.6–1.9 (4H, br m, CH$_2$(C$\underline{H}_2$)$_2$), 2.3–2.6 (4H, br m, C$\underline{H}_2$(CH$_2$)$_2$C$\underline{H}_2$), 3.76 (3H, s, O$\underline{Me}$), 6.4–6.5 (1H, br m, C$\underline{H}$═C), 6.65 (1H, d, J 8.5 Hz, Ar$\underline{H}$ ortho to OMe), 7.18 (1H, dd, J 8.5, 2.4 Hz, Ar$\underline{H}$ para to olefin), and 7.39 (1H, d, J 2.4 Hz, Ar$\underline{H}$ ortho to olefin).

INTERMEDIATE 13

5-Formyl-2-methoxybenzylidenecyclopentane n-BuLi (1.6$\underline{M}$ solution in hexane) (22 ml, 27.7 mmol, 1.1 equiv) was added dropwise at below −70° C. to a solution of Intermediate 12 (6.81 g, 25.5 mmol) in THF (50 ml). The resulting orange solution was stirred for a further 0.5 h then DMF (3.0 ml, 39 mmol, 1.5 equiv) was added at below −60° C. The reaction mixture was allowed to warm to RT, stirred for 1 h, then treated with hydrochloric acid (10%; 100 ml). After 1 h, the mixture was extracted with $CH_2Cl_2$ (150 ml, 2×50 ml). The extract was washed (brine; 50 ml), dried ($Na_2SO_4$), and concentrated in vacuo to give a yellow oil (7.0 g). The crude product was subjected to chromatography ($SiO_2$; $Et_2O$-hexane, 1:3) to afford the title compound (4.58 g) as a colourless oil δH (80 MHz; $CDCl_3$) 1.6–1.9 (4H, br m, $CH_2(CH_2)_2$), 2.4–2.65 (4H, br m, $CH_2(CH_2)_2CH_2$), 3.88 (3H, s, OMe), 6.45–6.6 (1H, br m, CH=C), 6.89 (1H, d, J 8.6 Hz, ArH ortho to OMe), 7.59 (1H, d, J 2.2 Hz, ArH ortho to olefin), 7.75 (1H, dd, J 8.6, 2.2 Hz, ArH para to olefin), and 9.81 (1H, s, CHO).

INTERMEDIATE 14

2-[2-Methoxy-5-(phenylhydroxymethyl)]-1,3-dioxane n-BuLi (1.6M solution in hexane) (115 ml, 184 mmol) was added dropwise at ca −70° C. to a solution of Intermediate 9 (50.3 g, 184 mmol) in THF (1000 ml). A solution of benzaldehyde (20.5 g, 193 mmol) in THF (100 ml) was added dropwise at ca −70° C. and the reaction mixture allowed to warm to RT over 3 h. The mixture was quenched with 10% aqueous $NH_4Cl$ solution (200 ml) and the organic layer separated and combined with EtOAc extracts (3×100 ml). The extract was dried ($MgSO_4$) and concentrated in vacuo to afford the title compound (61.0 g) as a pale yellow crystalline solid. δH ($CDCl_3$) 1.47 (1H, br d, J ca 13 Hz, $CH_2CHCH_2$), 2.15–2.35 (2H, complex m, $CH_2CHCH_2$+OH), 3.82 (3H, s, OMe), 3.99 (2H, ca. t, J ca. 11 Hz, $CHCH_2CH$), 4.23 (2H, dd, J ca. 11.4 Hz, $CHCH_2CH$), 5.81 (1H, s, ArCH), 5.85 (1H, s, ArCH), 6.83 (1H, d, J 8.6 Hz, ArH ortho to OMe), 7.2–7.4 (6H, m, $C_6H_5$+ArH para to dioxolane), and 7.68 (1H, d, J 2.3 Hz, ArH ortho to dioxolane).

INTERMEDIATE 15

[3-(2-Dioxan-1,3-yl)-4-methoxy]benzophenone

A mixture of Intermediate 14 (60.0 g, 200 mmol) and manganese dioxide (174 g, 2.0 mol) in $CH_2Cl_2$ (1000 ml) was stirred at RT for 18 h. The reaction mixture was filtered through Celite and the filtrate concentrated in vacuo. The residue was recrystallised from diisopropyl ether-toluene to afford the title compound (41.0 g) as a white solid. δH ($CDCl_3$) 1.41 (1H, br d, J 13.5 Hz, $CH_2CHCH_2$), 2.1–2.3 (1H, complex m, $CH_2CHCH_2$), 3.93 (3H, s, OMe), 3.99 (2H, dt, J 2.1, 12.3 Hz, $CHCH_2CH$), 4.23 (2H, dd, J 4.5, 11.5 Hz, $CHCH_2CH$), 5.87 (1H, s, ArCH), 6.94 (1H, d, J 8.6 Hz, ArH ortho to OMe), 7.4–7.6 (3H, m, meta and para $C_6H_5$), 7.75 (2H, d, J 8.4 Hz ortho $C_6H_5$), 7.84 (1H, dd, J 2.3, 8.6 Hz, ArH para to dioxane), and 8.15 (1H, dd, J 2.3 Hz, ArH ortho to dioxane).

INTERMEDIATE 16

(±)-1-{3-[2-(1,3-Dioxanyl)]-4-methoxyphenyl}-1-phenyl-2-(4-pyridyl)ethanol n-BuLi (2.5M solution in hexane) (55.6 ml, 139 mmol, 1.05 equiv.) was added to a solution of 4-methylpyridine (11.9 ml, 133 mmol) in THF (500 ml) at −70° C. The mixture was allowed to stir at −70° C. for 0.5 h then a solution of Intermediate 15 (40.0 g, 133 mmol) in THF (250 ml) was added dropwise and allowed to warm to RT overnight. The reaction mixture was quenched with 10% aqueous $NH_4Cl$ solution (100 ml) and extracted with $CH_2Cl_2$ (300 ml, 100 ml). The extract was separated, dried ($Na_2SO_4$), and concentrated in vacuo. The residue was recrystallised from EtOAc to afford the title compound (28.9 g) as a white crystalline solid δH ($CDCl_3$) 1.41 (1H, br d, J 13.5 Hz, $CH_2CHCH_2$), 2.15–2.25 (1H, complex m, $CH_2CHCH_2$), 2.4 (1H, br s, OH), 3.54 (1H, d, J 13.1 Hz, pyridine CH), 3.62 (1H, d, J 13.1 Hz, pyridine CH), 3.82 (3H, s, OMe), 3.99 (2H, dt, J 2.1, 12.3 Hz, $CHCH_2CH$), 4.23 (2H, dd, J 5.1,10.7 Hz, $CHCH_2CH$), 5.84 (1H, s, ArCH), 6.75–6.85 (3H, m, ArH meta/para to dioxane+$C_6H_5$ para H), 7.15–7.35 (6H, m pyridine $H_3,H_5$+$C_6H_5$ ortho/meta H), 7.76 (1H, d, J 2,3 Hz, ArH ortho to dioxane), and 8.30 (1H, dd, J 1.5, 4.5 Hz, pyridine $H_2,H_6$).

INTERMEDIATE 17

(E,Z)-4-{2-[3-(2-Dioxan-1,3-yl)-4-methoxyphenyl]ethenyl}pyridine

Trifluoroacetic anhydride (11.3 ml, 80.2 mmol) was added dropwise at ca. −10° C. to a solution of Intermediate 16 (28.59 g, 72.9 mmol) and triethylamine (15.2 ml, 109.3 mmol) in $CH_2Cl_2$ (500 ml). The reaction mixture was stirred at −10° C. for 0.5 h then quenched with 10% aqueous sodium carbonate solution (250 ml). The organic layer was separated and combined with further $CH_2Cl_2$ extracts (3×50 ml), then dried ($Na_2SO_4$) and concentrated in vacuo. The residue was subjected to chromatography ($SiO_2$; 5% MeOH $CH_2Cl_2$) to afford the title compound (20.0 g) as a yellow solid. δH ($CDCl_3$) ('Hnmr indicates ca 3:1 mixture of isomers; data for major isomer, possibly (E)-, presented) 1.43 (1H, br d, J 12.6 Hz, $CH_2CHCH_2$), 2.15–2.35 (1H, complex m, $CH_2CHCH_2$), 3.84 (3H, s, OMe), 4.01 (2H, ca. t, J 11.5 Hz, $CHCH_2CH$), 4.26 (2H, dd, J 4.9,11.5 Hz, $CHCH_2CH$), 5.88 (1H, s, ArCH), 6.77 (1H, d, J 8.6 Hz, ArH ortho to OMe), 6.81 (2H, d, J 5.8 Hz, pyridine $H_3$, $H_5$), 6.85 (1H, s, C=CH), 7.03 (1H, dd, J 2.3, 8.6 Hz, ArH para to dioxane), 7.1–7.2 (2H, m, $C_6H_3H_2$), 7.3–7.35 (3H, m, $C_6H_3H_2$), 7.83 (1H, d, J 2.4 Hz, ArH ortho to dioxane) and 8.30 (2H, d, J 5.8 Hz, pyridine $H_2,H_6$).

INTERMEDIATE 18

2-Methoxy-5-[1-phenyl-2-(4-pyridyl)ethyl]benzaldehyde

A solution of Intermediate 17 (17.5 g, 46.8 mmol) in THF-MeOH (5:1; 1200 ml) containing 10% Pd/C (0.5 g) was hydrogenated at RT over 1 h. The reaction mixture was filtered through Celite and then concentrated in vacuo. The crude alkane (15.0 g) in THF (750 ml) and 10% hydrochloric acid (75 ml) was vigorously stirred at RT for 0.5 h, then quenched with aqueous $NaHCO_3$ (2M; 100 ml). The organic solvent was removed in vacuo and the aqueous phase extracted with EtOAC (3×100 ml). The extract was dried ($MgSO_4$) and concentrated in vacuo to afford the title compound (12.6 g). δH ($CDCl_3$) 3.34 (2H, d, J 8.0 Hz, $CHCH_2$pyridine), 3.87 (3H, s, OMe), 4.22 (1H, t, J 8.0 Hz, $CHCH_2$pyridine), 6.87 (1H, d, J 8.6 Hz, ArH ortho to OMe), 6.92 (2H, d, J 6.0 Hz, $H_2$, $H_6$ of $C_6H_5$), 7.1–7.3 (5H, m, pyridine $H_3$, $H_5$+$H_3$, $H_4$, $H_5$ of $C_6H_5$), 7.32 (1H, dd,J 2.4, 8.6 Hz, ArH para to CHO), 7.74 (1H, d, J 2.4 Hz, ArH ortho to CHO), 8.38 (2H, ca. d, J 4.5 Hz, pyridine $H_2,H_6$) and 10.42 (1H, s, ArCHO).

INTERMEDIATE 19

(±)-4-[2-(3-Cyclopentyloxy-4-methoxyphenyl)-2-hydroxyethyl]pyridine

The title compound was prepared as described in the International Patent Application No. WO94/20446.

INTERMEDIATE 20

(E)-4-[2-(3-Cyclopentyloxy-4-methoxyphenyl)ethenyl]pyridine

The title compound was prepared as described in the International Patent Application No. WO94/20446.

INTERMEDIATE 21

5-Phentylpentylbromide

To a stirred solution of 5-phenyl-1-pentanol (2.80 g, 17.07 mmol) in dry $CH_2Cl_2$ (80 ml) at 0° C. under a nitrogen atmosphere was added $PBr_3$ (4.62 g, 1.62 ml. 17.07 mmol). The mixture was stirred at RT for 34 min and quenched cautiously with saturated $NaHCO_3$ solution (100 ml). The layers were separated and the aqueous layer extracted with $CH_2Cl_2$ (2×60 ml). The combined organic extract was washed with water (80 ml), dried ($MgSO_4$)and the residue subjected to chromatography ($SiO_2$) to give the title compound (0.69 g) as a clear oil.

EXAMPLE 1 a) (R)-4-[2-(3-Benzyloxy-4-methoxyphenyl)-2-phenylethyl]pyridine

Potassium tert-butoxide (180 mg, 1.57 mmol) was added to a stirred solution of Intermediate 7 (400 mg, 1.31 mmol) in THF (15 ml) and DMF (5 ml). The mixture was stirred at RT for 0.25 h then treated with benzyl bromide (246 mg, 1.44 mmol). After 0.5 h at RT, the reaction mixture was quenched with water (5 ml) and concentrated in vacuo. The residue was partitioned between water (20 ml) and EtOAc (30 ml). The organic layer was separated and combined with further EtOAC extracts (2×30 ml). The extract was dried ($MgSO_4$) and concentrated in vacuo to give a pale brown oil which was subjected to chromatography ($SiO_2$; EtOAc-hexane, 17:3) to afford the title compound (434 mg) as a colourless oil δH ($CDCl_3$) 3.18 (1H, dd, J 13.6, 8.4 Hz, CHC$\underline{H}_A H_B$), 3.25 (1H, dd, J 13.6, 7.4 Hz, CHCH$_A\underline{H}_B$), 3.84 (3H, s, O$\underline{Me}$), 4.09 (1H, t, J 7.9 Hz, C$\underline{H}$CH$_A H_B$), 5.08 (2H, s, OC$\underline{H}_2$), 6.58–6.8 (3H, m, C$_6\underline{H}_3$), 6.82 (2H, dd, J 4.5, 1.6 Hz, pyridine $\underline{H}_3$, $\underline{H}_5$), 7.05–7.4 (10H, m, 2×C$_6\underline{H}_5$), and 8.35 (2H, dd, J 4.5,1.6 Hz, pyridine $\underline{H}_2$,$\underline{H}_6$).

The following Example was prepared in a manner similar to compound of Example 1a).

b) 4-{2-(R)-[4-Methoxy-3-(phenylpentyloxy)phenyl]-2-phenylethyl}pyridine

From Intermediate 7a) (0.29 g, 0.95 mmol) in THF (5 ml) and DMF (3 ml), potassium tert-butoxide (0.12 g, 1.04 mmol) and 5-phenylbromopentane (0.26 g, 1.14 mmol) in THF (5 ml). Chromatography ($SiO_2$; EtOAc-hexane, 1:1) gave the title compound (0.33 g) as a clear colourless oil. (Found C, 82.16; H, 7.38; N, 3.06. $C_{31}H_{33}NO_2$ requires C, 82.45; H, 7.37; N, 3.10%) δH (300 MHz; $CDCl_3$) 1.40–1.85 (6H, m, (C$\underline{H}_2$)$_3$), 2.63 (2H, t, J 7.6 Hz, $C_6H_5$C$\underline{H}_2$), 3.31 (2H, d, J 7.9 Hz, C$\underline{H}_2$ pyridine), 3.81 (3H, s, OC$\underline{H}_3$), 3.90 (2H, dt, J 6.8, 1.6 Hz, OC$\underline{H}_2$), 4.15 (1H, t, J 9 Hz, $CH_2$C$\underline{H}$), 6.65 (1H, d, J 1.8 Hz, Ar$\underline{H}_2$), 6.7–6.8 (2H, m, ArH), 6.92 (2H, dd, J 4.6, 1.4 Hz, pyridine $\underline{H}_3$, $\underline{H}_5$), 7.15–7.30 (10H, m, 2×C$_6\underline{H}_5$), and 8.38 (2H, dd, J 4.5, 1.5 Hz, $\underline{H}_2$,$\underline{H}_6$ pyridine).

c) (E)-4-[4-Methoxy-3-(5-phenylpentyloxy)phenylethenyl]pyridine

From Intermediate 7b) (0.68 g, 3.0 mmol) potassium t-butoxide (0.40 g, 3.6 mmol) and Intermediate 21 (0.68 g, 3.0 mmol). Chromatography ($SiO_2$; EtOAc-hexane, 3:1) gave a slightly off-white solid (0.874 g). A small portion (0.34 g) was recrystallised (diisopropylether; 9 ml) to give the title compound (0.312 g) as an amorphous white solid (0.312 g). m.p. 98–100° C. (Found C, 80.31; H, 7.27; N, 3.56. $C_{25}H_{27}NO_2$ requires C, 80.40; H, 7.29; N, 3.7%). δH (300 MHz; $CDCl_3$) 1.5–2.0 (6H, m, (C$\underline{H}_2$)$_3$), 2.67 (2H. t. J 7.7 Hz, ArC$\underline{H}_2$), 3.89 (3H, s, OC$\underline{H}_3$), 4.07 (2H, t, J 6.8 Hz, OC$\underline{H}_2$), 6.86 (1H, d, J 16.3, $\underline{H}$C=C), 6.88 (1H, d, J 8.9 Hz, ArH), 7.07–7.31 (6H, m, ArH and $\underline{H}$C=C), 7.33 (2H, dd, J 4.6, 1.5 Hz, pyridine $\underline{H}_3$, $\underline{H}_5$) and 8.55 (2H, dd, J 4.6, 1.5 Hz pyridine $\underline{H}_2$,$\underline{H}_6$).

EXAMPLE 2 a) (R)-4-[2-(4-Methoxy-3-(3-thienyloxy)phenyl)-2-phenylethyl]pyridine

A mixture of Intermediate 7a) (500 mg, 1.64 mmol), anhydrous potassium carbonate (450 mg, 3.28 mmol) and 3-bromothiophene (3.48 g, 21.3 mmol) in pyridine (4 ml) was heated to ca. 90° C. Copper (II) oxide (330 mg, 4.1 mmol) was added and the reaction mixture heated to reflux for 52 h. $CH_2Cl_2$ (20 ml) was added to the cooled reaction mixture which was then filtered. The filtrate was concentrated in vacua and the residue subjected to chromatography ($SiO_2$; EtOAc-hexane, 17:3) to afford the title compound (315 mg), as a colourless oil. (Found C, 74.15; H, 5.40; N, 3.50. $C_{24}H_{21}NO_2S$ requires C, 74.39; H, 5.46; N, 3.61%) δH ($CDCl_3$) 3.24 (1H, dd, J 13.6, 8.5 Hz, CH×C$\underline{H}_A H_B$), 3.30 (1H, dd, J 13.6, 7.4 Hz, CH×CH$_A\underline{H}_B$), 3.81 (3H, s, OMe), 4.14 (1H, t, J ca. 8.0 Hz, C$\underline{H}$×CH$_A H_B$), 6.28 (1H, dd, J 3.3, 1.5 Hz, thiophene $\underline{H}$), 6.74 (1H, dd, J 5.2, 1.5 Hz, thiophene $\underline{H}$), 6.8–6.95 (5H, m), 7.1–7.3 (6H, m), and 8.39 (2H, br s, pyridine $\underline{H}_2$,$\underline{H}_6$).

The following Examples were prepared in a manner similar to compound of Example 2a).

b) 4-{2-(R)-[3(4Biphenyloxy)-4-methoxyphenyl)-2-phenyl]ethyl}pyridine

From Intermediate 7a) (0.4 g, 1.131 mmol), anhydrous potassium carbonate (0.36 g, 2.62 mmol), 4-bromobiphenyl (0.4 g, 1.70 mmol) and copper (II) oxide (0.26 g, 3.3 mmol). Chromatography ($SiO_2$; EtOAc-hexane, 1:1 then 7:3) gave the title compound (0.383 g) as a clear colourless oil. (Found C, 83.40; H, 5.89; N, 3.03. $C_{32}H_{27}NO_2$ requires C, 83.92; H, 5.95; N, 3.06%). δH (300 MHz; $CDCl_3$) 3.25 (1H, dd, J 13.6, 8.5 Hz, pyridine CH$_A\underline{H}_B$), 3.25 (1H, dd, J 13.6, 7.5 Hz, pyridine C$\underline{H}_A H_B$), 3.80 (3H, s, OC$\underline{H}_3$), 4.16 (1H, t, $C_6H_3$C$\underline{H}$), 6.85–7.0 (7H, m, Ar$\underline{H}$, pyridine $\underline{H}_3$, $\underline{H}_5$), 7,15–7.6 (12H, m, Ar$\underline{H}$) and 8.40 (2H, br s, pyridine $\underline{H}_2$,$\underline{H}_6$).

c) 4-[2-(R)-(4-Methoxy-3-phenyloxyphenyl)-2-phenylethyl]pyridine

From Intermediate 7a) (0.4 g, 1.31 mmol), anhydrous potassium carbonate (0.36 g, 2.62 mmol), bromobenzene (2.98 g, 2.0 ml, 19 mmol) and copper (II) oxide (0.26 g, 3.3 mmol). Chromatography ($SiO_2$; EtOAc-hexane, 17:3) gave the title compound (0.433 g) as a clear oil. (Found C, 81.45; H, 5.97; N, 3.48. $C_{26}H_{32}NO_2$ requires C, 81.86; H, 6.08; N, 3.67%). δH (300 MHz; $CDCl_3$) 3.24 (1H, dd, J 13.6, 8.7 Hz, pyridine CH$_A\underline{H}_B$), 3.29(1H, dd, J 13.6, 7.4 Hz, pyridine C$\underline{H}_A H_B$), 3.78 (3H, s, OC$\underline{H}_3$), 4.14 (1H, t, J 7.9 Hz, C$H_2$C$\underline{H}$), 6.80–6.94 (7H, m, Ar$\underline{H}$, pyridine $\underline{H}_3$, $\underline{H}_5$), 7.00–7.06 (1H, m, Ar$\underline{H}$), 7,15–7.3 (7H, m, Ar$\underline{H}$) and 8.39 (2H, dd, J 4.5, 1.6 Hz, pyridine $\underline{H}_2$,$\underline{H}_6$).

EXAMPLE 3

(2R)-4-[2-(3-((2RS)-exo-Bicyclo[2.2.1]hept-2-yloxy)-4-methoxyphenyl)-2-phenylethyl]pyridine Diethylazodicarboxylate (522 mg, 3.0 mmol) was added to a mixture of Intermediate 7a) (610 mg, 2.0 mmol), (±)-endo-2-norborneol (224 mg, 2.0 mmol), and triphenylphosphine (787 mg, 3.0 mmol) in THF (5 ml) and the mixture heated to reflux for 40 h. The reaction mixture was poured into saturated $NaHCO_3$ solution (10 ml) and extracted with $CH_2Cl_2$ (2×25 ml). The extract was dried ($Na_2SO_4$), concentrated in vacuo, and then subjected to chromatography ($SiO_2$; $Et_2O$) to afford the title compound (256 mg) as a colourless oil. δH ($CDCl_3$) 1.0–1.75 (8H, m, norbornyl H's), 2.2–2.4 (2H, br m, norbornyl H's), 3.25–3.4 (2H, m, CHCH$_2$), 3.77 (3H, s, OMe), 4.05 (1H, br d, J 5.6 Hz, OCH), 4.14 (1H, t, J 7.9 Hz, CHCH$_2$), 6.6–6.8 (3H, m, $C_6H_3$), 6.92 (2H, ca. d, J 4.5 Hz, pyridine $H_3$, $H_5$), 7.1–7.3 (5H, m, $C_6H_5$), 8.38 (2H, ca.d, J 4.5 Hz, pyridine $H_2$,$H_6$); m/z (EI) 399 ($M^+$, 8%), 307 (13), 305 (18), 213 (100), 152 (18), 95 (51), 93 (19), and 67 (37).

EXAMPLE 4 a) 3-(3-Cyclopentylidenyl-4-methoxyphenyl) pyridine hydrochloride

To a solution of cyclopentyl triphenylphosphonium bromide (3.66 g, 8.9 mmol) in THF (50 ml) was added dropwise n-BuLi (1.6M in hexane) (5.6 ml, 9.0 mmol) at 0° C. The red solution was stirred and left to warm up to RT for 1 h then treated with a solution of Intermediate 8 (1.9 g, 8.9 mmol) in THF (25 ml) at 0° C. After stirring for 1 h at RT the reaction mixture was quenched with water (50 ml) and extracted with $CH_2Cl_2$ (1×75, 1×50, 1×25 ml). The extract was washed (brine), dried ($Na_2SO_4$) and concentrated in vacuo to give a colourless syrup which crystallised to give a white solid. Purification by column chromatography [$SiO_2$; EtOAc] furnished the title compound free base (1.80 g) as a white solid.

A portion of the free base (388 mg) was treated with ethanolic HCl and diluted with a little $Et_2O$. The precipitate was decanted, washed ($Et_2O$) and dried in vacuo to furnish the title compound (420 mg) as a pale yellow solid (Found: C, 71.56; H, 6.68; N, 4.74. $C_{18}H_{19}NO$. HCl requires C, 71.63; H, 6.68; N, 4.64%). δH (80 MHz; $CDCl_3$) 1.6–1.9 (4H, br m, $CH_2(CH_2)_2CH_2$), 2.4–2.65 (4H, br m, CH$_2$(CH$_2$)$_2$CH$_2$), 3.89 (3H, s, OMe), 6.5–6.6 (1H, br m, HC=C), 6.97 (1H, d, J 8.6 Hz, ArH ortho to OMe), 7.40 (1H, dd, J 8.6, 2.2 Hz, ArH para to C=C), 7.53 (1H, d J 2.2 Hz, ArH ortho to C=C), 7.9 (1H, dd, J 5.6, 8.3 Hz, pyridine $H_5$), 8.4–8.7 (2H, m, pyridine $H_4$, $H_6$) and 8.85 (1H, d, J 2.2 Hz, pyridine $H_2$).

b) 4-[2-(3-Cyclopentylidenylmethyl-4-methoxyphenyl)2-phenylethyl]pyridine hyrochloride hemihydrate From n-BuLi (1,6M solution in hexane) (2.1 ml, 3.55 mmol, 1.06 equiv), cyclopentyltriphenylphosphonium bromide (1.43 g, 3.46 mmol, 1.1 equiv) in THF (30 ml) and Intermediate 18 (1.00 g, 3.15 mmol) in THF (20 ml). Chromatography ($SiO_2$; 2% MeOH—$CH_2Cl_2$) afforded the title compound free base (420 mg). δH ($CDCl_3$) 1.6–1.8 (4H, br m, CH$_2$(CH$_2$)$_2$CH$_2$), 2.2–2.35 (2H, br m, CH(CH$_2$)$_2$CH), 2.4–2.55 (2H, br m, CH(CH$_2$)$_2$CH), 3.22 (2H, d, J 7.8 Hz, CHCH$_2$ pyridine), 3.78 (3H, s, OMe), 4.17 (1H, t, J 7.8 Hz, CHCH$_2$ pyridine), 6.51 (1H, ca. t, J 2.2 Hz, HC=CH$_2$), 6.72 (1H, d, J 8.4 Hz, ArH ortho to OMe), 6.85–7.0 (3H, m, Hof $C_6H_3$+pyridine $H_3$, $H_5$), 7.1–7.3 (6H, m, $C_6H_5$+Hof $C_6H_3$) and 8.38 (2H, ca. d, J 5.7 Hz, pyridine $H_2$, $H_6$).

The base (420 mg) was dissolved in $Et_2O$ (5 ml) and treated dropwise with ethanolic HCl. The precipitated product was collected by filtration and dried in vacuo to afford the title compound as a white solid (Found: C, 75.23; H, 6.72; N, 3.11; $C_{26}H_{28}NO$. 0.5$H_2O$ requires C, 75.25; H, 7.04; N, 3.38%). δH ($CDCl_3$) 1.6–1.8 (4H, br m, CH$_2$(CH$_2$)$_2$CH$_2$), 2.2–2.35 (2H, br m, CH(CH$_2$)$_2$CH), 2.4–2.55 (2H, br m, CH(CH$_2$)$_2$CH), 3.59 (2H, d, J 8.0 Hz, CHCH$_2$ pyridine), 3.80 (3H, s, OMe), 4.18 (1H, t, J 8.0 Hz, CHCH$_2$ pyridine), 6.51 (1H, ca. t, J 2.0 Hz, CH=CCH$_2$), 6.73 (1H, d, J 8.4 Hz, ArH ortho to OMe), 6.87 (1H, dd, J 2.2, 8.4 Hz, ArH para to olefin), 7.1–7.45 (6H, m, $C_6H_5$+ArH ortho to olefin), 7.46 (2H, ca. d, J ca. 6.4 Hz, pyridine $H_3$, $H_5$), and 8.50 (2H, ca. d, J ca. 6.4 Hz, pyridine $H_2$, $H_6$); m/z (ESI) 370 ($M^+$+1-HCl, 18%), 369 ($M^+$-HCl, 95), 277 (100), 178 (55), 165 (75), and 152 (45).

c) 4-[2-(3-Cyclohexylidenylmethyl-4-methoxyphenyl)-2-phenyl-ethyl]pyridine hydrochloride From Intermediate 18 (1.00 g, 3.15 mmol), cyclohexyltriphenylphosphonium bromide (1.47 g, 3.46 mmol, 1.1 equiv) and n-BuLi (1.6 M solution in hexane) (2.1 ml, 3.36 mmol, 1.07 equiv). The crude product was subjected to chromatography ($SiO_2$; 2% MeOH—$CH_2Cl_2$) to afford the title compound free base (1.07 g).

A portion of the free base (400 mg) was dissolved in $Et_2O$ (5 ml) and treated with ethanolic HCl to afford the title compound as a white solid (Found: C, 77.32; H, 7.15; N, 3.24. $C_{27}H_{30}ClNO$ requires C, 77.21; H, 7.20; N, 3.34%). δH ($CDCl_3$) 1.4–1.75 (6H, br m, CH$_2$(CH)$_3$CH$_2$), 2.0–2.1 (2H, br m, CH(CH$_2$)$_3$CH), 2.2–2.3 (2H, br m, CH(CH$_2$)$_3$CH), 3.58(2H, d, J 8.0 Hz, CHCH$_2$ pyridine), 3.78 (3H, s, OMe), 4.18 (1H, t, J 8.0 Hz, CHCH$_2$ pyridine), 6.15 (1H, ca. s, HC=CCH$_2$), 6.73 (1H, d, J 9.0 Hz, ArH ortho to OMe), 6.85–6.95 (2H, m, ArH), 7.1–7.35 (5H, m, ArH), 7.46 (2H, d, J 5.8 Hz, pyridine H3, $H_5$), and 8.50 (2H, d, J 5.8 Hz, pyridine $H_2$, $H_6$); m/z (ESI) 384 ($M^+$+1-HCl, 37%), 383 ($M^+$-HCl, 85), 291 (100), 178 (32), 165 (50), 152 (28) and 91 (33).

d) 4-{2(R)-[3-(Phenyl-1,3-butedienyl)-4-methoxyphenyl]-2-phenylethyl}pyridine

From n-BuLi (1.6M solution in hexane) (1.2 ml, 2.93 mmol, 1.05 equiv). cinnamyltriphenylphosphonium bromide (930.6 mg, 2.02 mmol) and Intermediate 9 (583.9 mg, 1.84 mmol). Chromatography ($SiO_2$; EtOAc-hexane, 1:1) gave the title compound.

EXAMPLE 5 a) 3-(3-Cyclopentylmethyl-4-methoxyphenyl) pyridine hydrochloride

The compound of Example 4a) (485 mg) was hydrogenated over the weekend in EtOH (25 ml) in the presence of 5% Pd/C (50 mg). The reaction mixture was filtered through Celite and concentrated in vacuo to give the title compound free base (464 mg) as a colourless oil.

The free base was dissolved in warm ethanolic HCl, precipitated with $Et_2O$, decanted and dried in vacuo to yield the title compound (485 mg) as a white solid. (Found: C, 70.98; H, 7.31; N, 4,62. $C_{18}H_{21}NO$. HCl requires C, 71.16; H, 7.30; N, 4.61%). δH (80 MHz; $CDCl_3$) 1.5–1.8 ((H, v.br m, cyclopentyl H's), 2.67 (2H, d, J 6.8 Hz,CH$_2$ cyclopentyl), 3.87 (3H, s, OMe), 6.95 (1H, d, J 8.0 Hz, ArH ortho to OMe), 7.35–7.50 (2H, m, 2×ArH meta to OMe), 7.8–8.0 (1H, m, pyridine $H_5$), 8.4–8.65 (2H, m, pyridine H) and 8.87 (1H, ~d, J 2.0 Hz, pyridine $H_2$).

The following compound was prepared in a manner similar to the compound of Example 5a).

b) 4-{2-[4-Methoxy-3-(5-phenylpentyloxy) phenylethyl}pyridine

From the compound of Example 1c) (0.534 g, 1.43 mmol) and 5% Pd/C catalyst (40 mg). Chromatography (SiO$_2$; EtOAc-hexane, 3:1) gave a clear colourless oil which solidified to give the title compound (0.45 g) as a white amorphous solid. m.p. 59–62° C. (Found C, 79.63; H, 7.79; N, 3.57. $C_{25}H_{29}NO_2$ requires C, 79.96; H, 7.78; N, 3.73%) δH (300 MHz; CDCl$_3$) 1.4–1.9 (6H, br m, (C$\underline{H}_2$)$_3$), 2.65 (2H, t, J 7.7 Hz, ArC$\underline{H}_2$), 2.83–2.91 (4H, m, (C$\underline{H}_2$)$_2$), 3.83 (3H, s, OC$\underline{H}_3$), 3.94 (2H, t, J 6.8 Hz, OC$\underline{H}_2$), 6.63 (1H, d, J 2.0 Hz, Ar$\underline{H}_2$), 6.66 (1H, dd, J 8.0, 2.0 Hz, Ar$\underline{H}$6), 6.78 (1H, d, J 8.1 Hz, Ar$\underline{H}_4$), 7.06 (2H, dd, J 4.4, 1.6 Hz, pyridine $\underline{H}$3, $\underline{H}_5$), 7.15–7.3 (5H, m, ArH), and 8.47 (2H, dd, J 4.4, 1.6 Hz, pyridine $\underline{H}_2$, $\underline{H}_6$).

c) 4-[2-(4-Methoxy-3-butylphenyl)-2-phenylethyl] pyridine hydrochloride

From the compound of Example 4d). Chromatography (SiO$_2$; EtOAc-hexane, 1:9) gave the title compound free base as a colourless oil. The free base was treated with ethanolic HCl to give the title compound as an off-white solid. (Found C, 78.13; H, 6.98; N, 3.02 $C_{30}H_{32}NOCl$ requires C, 78.67; H, 7.04; N, 3.06%). δ$_H$ (CDCl$_3$) 1.55 (4H, m, CH$_2$(C$\underline{H}_2$)CH$_2$), 2.60 (4H, m, C$\underline{H}_2$(CH$_2$)$_2$CH$_2$), 3.55 (2H, d, pyridine (C$\underline{H}_2$), 3.75 (3H, S, OC$\underline{H}_3$), 4.15 (1H, t, ArC $\underline{H}$), 6.70 (m, ArH), 6.90 (2H, m, ArH), 7.10–7.30 (10H, m, 2×C$_6\underline{H}_5$), 7.4 (2H, d, ArH) and 8.55 (2H, d, ArH).

EXAMPLE 6

Methyl 3-[Cyclopentylidenyl-4-methoxyphenyl] propenoate

A mixture of trimethylphosphonoacetate (2.7 g, 14.8 mmol) and Intermediate 13 (3.009, 13.9 mmol) in MeOH (30 ml) was added to a solution of sodium methoxide [prepared from sodium (0.4 g, 17.4 mmol) in MeOH (50 ml) at RT]. The reaction mixture was stirred at RT overnight then the crystalline product collected by filtration, washed with MeOH (2×10 ml), and dried in vacuo to afford the title compound (2.70 g) as a white solid (Found: C, 74.73; H, 7.43 $C_{17}H_{20}O_3$ requires: C, 74.97; H, 7.40%); δH (80 MHz; CDCl$_3$) 1.5–1.8 (4H, br m, CH$_2$(C$\underline{H}_2$)$_2$), 2.4–2.6 (4H, br m, C$\underline{H}_2$(CH$_2$)$_2$C$\underline{H}_2$), 3.77 (3H, s, OMe), 6.25 (1H, d, J 15.8 Hz, C$\underline{H}$=CH), 6.45–6.55 (1H, br m, C$\underline{H}$=CCH$_2$), 6.80 (1H, d, J 8.7 Hz, Ar$\underline{H}$ ortho to OMe), 7.28 (1H, dd, J 8.7, 2.6 Hz, Ar $\underline{H}$ para to cyclopentylidene), 7.48 (1H, d, J 2.6 Hz, Ar$\underline{H}$ ortho to cyclopentylidene), and 7.61 (1H, d, J 15.8 Hz, CH=C$\underline{H}$); m/z (El) 273 (M$^+$+1, 18%), 272 (100), 241 (11), 239 (11), 225 (11), 205 (19), 192 (17), 175 (11), 161 (17), and 115 (18).

The activity and selectivity of compounds according to the invention was demonstrated in the following tests. In these tests the abbreviation FMLP represents the peptide N-formyl-met-leu-phe.

1. Isolated Enzyme

The potency and selectivity of the compounds of the invention was determined using distinct PDE isoenzymes as follows:
i. PDE I, rabbit heart
ii. PDE II, rabbit heart
iii. PDE III, rabbit heart, Jurkat cells
iv. PDE IV, HL60 cells, rabbit brain, rabbit kidney and human recombinant PDE IV
v. PDE V, rabbit lung, guinea pig lung A gene encoding human PDE IV has been cloned from human monocytes (Livi, et al., 1990, *Molecular and Cellular Biology*, 10, 2678). Using similar procedures we have cloned human PDE IV genes from a number of sources including eosinophils, neutrophils, lymphocytes, monocytes, brain and neuronal tissues. These genes have been transfected into yeast using an inducible vector and various recombinant proteins have been expressed which have the biochemical characteristics of PDE IV (Beavo and Reifsnyder, 1990, *TIPS*, 11, 150). These recombinant enzymes, particularly the human eosinophil recombinant PDE IV, have been used as the basis of a screen for potent, selective PDE IV inhibitors.

The enzymes were purified to isoenzyme homogeneity using standard chromatographic techniques.

Phosphodiesterase activity was assayed as follows. The reaction was conducted in 150 μl of standard mixture containing (final concentrations): 50 mM 2-[[tris (hydroxymethyl)methyl]amino]-1-ethanesulphonic acid (TES) —NaOH buffer (pH 7.5), 10 mM MgCl$_2$, 0.1 μM [$^3$H]-cAMP and vehicle or various concentrations of the test compounds. The reaction was initiated by addition of enzyme and conducted at 30° C. for between 5 to 30 min. The reaction was terminated by addition of 50 μl 2% trifluoroacetic acid containing [$^{14}$C]-5'AMP for determining recovery of the product. An aliquot of the sample was then applied to a column of neutral alumina and the [$^3$H]-cAMP eluted with 10 ml 0.1 TES-NaOH buffer (pH8). The [$^3$H]-5'-AMP product was eluted with 2 ml 2M NaOH into a scintillation vial containing 10 ml of scintillation cocktail. Recovery of [3H]-5'AMP was determined using the [$^{14}$C]-5'AMP and all assays were conducted in the linear range of the reaction.

Compounds according to the invention such as compounds of the Examples herein cause a concentration-dependent inhibition of recombinant PDE IV at 0.1–1000 nM with little or no activity against PDE I, II, III or V at concentrations up to 100 μM.

2. The Elevation of cAMP in Leukocytes

The effect of compounds of the invention on intracellular cAMP was investigated using human neutrophils or guinea pig eosinophils. Human neutrophils were separated from peripheral blood, incubated with dihydrocytochalasin B and the test compound for 10 min and then stimulated with FMLP. Guinea pig eosinophils were harvested by peritoneal lavage of animals previously treated with intra-peritoneal injections of human serum. Eosinophils were separated from the peritoneal exudate and incubated with isoprenaline and test compound. With both cell types, suspensions were centrifuged at the end of the incubation, the cell pellets were resuspended in buffer and boiled for 10 min prior to measurement of cAMP by specific radioimmunoassay (DuPont).

The most potent compounds according to the Examples induced a concentration-dependent elevation of cAMP in neutrophils and/or eosinophils at concentrations of 0.1 nM to 1 μM.

3. Suppression of Leukocyte Function

Compounds of the invention were investigated for their effects on superoxide generation, chemotaxis and adhesion of neutrophils and eosinophils. Isolated leukocytes were incubated with dihydrocyto-chalasin B for superoxide generation only and test compound prior to stimulation with FMLP. The most potent compounds of the Examples caused a concentration-dependent inhibition of superoxide generation, chemotaxis and adhesion at concentrations of 0.1 nM to 1 μM.

Lipopolysaccharide (LPS)-induced synthesis of tumour necrosis factor (TNF) by human peripheral blood monocytes (PBM) is inhibited by compounds of the Examples at concentrations of 0.01 nM to 10 μM.

4. Adverse Effects

In general, in our tests, compounds of the invention have had no observed toxic effects when administered to animals at pharmacologically effect doses.

What is claimed is:

1. A compound of formula (1)

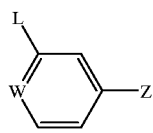

(1)

wherein

=W— is (1) =C(Y)— or (2) =N—;

L is (1) —C(R)=C($R^1$)($R^2$) or —(CHR)$_n$CH($R^1$)($R^2$), (2) —($X^a$)$_n$Alk'Ar' or —Alk'$X^a$Ar' or (3) $X^a$R';

Z is a group (A), (B), (C) or (D):

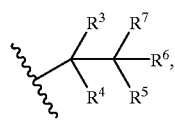

(A)

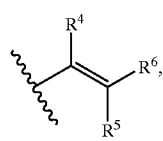

(B)

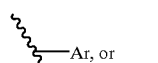

(C)

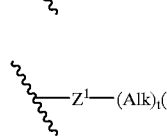

(D)

n is zero or the integer 1;

t is zero or an integer 1, 2 or 3;

Y is halogen or an alkyl or —$XR^a$ group;

each of X and $X^a$ is independently —O—, —S(O)$_m$—, or —N($R^b$)—;

$Z^1$ is —$NR^{12}$C(O)—, —C(O)$NR^{12}$—, —$NR^{12}$C(S)—, —C(S)$NR^{12}$—, —C≡C—, —$NR^{12}$SO$_2$— or —SO$_2$$NR^{12}$—;

m is zero or an integer 1 or 2;

each of $R^a$ and $R^b$ is independently hydrogen or an optionally substituted alkyl group;

R' is Ar' or an optionally substituted polycycloalkyl or polycycloalkenyl group optionally containing one or more —O— or —S— atoms or —N($R^b$)— groups;

Ar is an optionally substituted monocyclic or bicyclic aryl group optionally containing one or more heteroatoms selected from oxygen, sulphur and nitrogen atoms;

Ar' is an optionally substituted heterocycloaliphatic group or an optionally substituted monocyclic or bicyclic aryl group optionally containing one or more heteroatoms selected from oxygen, sulfur and nitrogen atoms;

Alk is an optionally substituted straight or branched alkylene chain optionally interrupted by an atom or group X;

Alk' is an optionally substituted straight or branched alkylene, alkenylene or alkynylene chain optionally interrupted by one or more linker atoms or groups $L^1$;

R is hydrogen, fluorine or a methyl group;

each of $R^1$ and $R^2$, which may be the same or different, is hydrogen, fluorine, —CN, —NO$_2$, or an optionally substituted alkyl, alkenyl, alkynyl, alkoxy, alkylthio, —CO$_2$$R^8$, —CONR$^9$R$^{10}$ or —CSNR$^9$R$^{10}$ group, or $R^1$ and $R^2$, together with the carbon atom to which they are attached, are linked to form an optionally substituted cycloalkyl, cycloalkenyl or heterocycloaliphatic group;

$R^3$ is hydrogen, fluorine, an optionally substituted straight or branched alkyl group, or —$OR^{11}$;

$R^4$ is hydrogen, —CN, —CH$_2$CN or an optionally substituted —CO$_2$$R^8$, —CSNR$^9$R$^{10}$ or —(CH$_2$)$_t$Ar group;

$R^5$ is —(CH$_2$)$_t$Ar;

$R^6$ is hydrogen, fluorine, —CO$_2$$R^8$, —CONR$^9$R$^{10}$, —CSNR$^9$R$^{10}$, or an optionally substituted alkyl group;

$R^7$ is hydrogen, fluorine, an optionally substituted straight or branched alkyl group, or —$OR^c$, where $R^c$ is hydrogen, formyl or an optionally substituted alkyl, alkenyl, alkoxyalkyl, alkanoyl, carboxamido or thiocarboxamido group;

each of $R^8$, $R^9$ and $R^{10}$ is independently hydrogen or an optionally substituted alkyl, aralkyl or aryl group;

$R^{11}$ is hydrogen, formyl or an optionally substituted alkyl, alkenyl, alkoxyalkyl, alkanoyl, carboxamido or thiocarboxamido group;

$R^{12}$ is hydrogen or an optionally substituted alkyl or —(Alk)$_t$Ar group; and the salts, solvates, hydrates, prodrugs and N-oxides thereof;

with the provisos that when L is a group (2) or (3), then Z is a group (A) or (B) in which $R^4$ is —(CH$_2$)$_t$Ar, when W is =N—, L is methyl, Z is a group (A) or (B) and $R^5$ is phenyl, then at least one of $R^3$, $R^4$, $R^6$ and $R^7$ is other than hydrogen within the atoms or groups defined for $R^3$, $R^4$, $R^6$ $R^7$ hereinabove, when W is =N—, L is methyl, Z is a group (D), $Z^1$ is —C(O)NH— and Ar is phenyl, then n is 1 and/or t is 1, 2 or 3, when W is C(OCH$_3$), L is bicyclo(2.2.1) heptyloxy, Z is a group (B), and $R^4$ and $R^6$ are hydrogen, then $R^5$ is other than 4-(methoxycarbonyl)phenyl within the groups defined for $R^5$ hereinabove, when W is C(OCH$_3$), L is [exo-8,9,10-trinorbornyl-2-oxy] tricycloalkyloxy or benzyloxy, Z is a group D, $Z^1$ is —C(O)NH— and Ar is 3,5-dichloropyrid-4-yl, 2,6-dichlorophenyl or unsubstituted phenyl, then n is 1 and/or t is 1, 2 or 3, and when W is C(OCH$_3$) and L is benzyloxy, then Z is other than a group (C) in which Ar is an optionally substituted nitrogen-containing monocyclic or bicyclic heterocycle within the groups defined for Ar hereinabove.

2. A compound according to claim 1 wherein W is a =C(Y)— group.

3. A compound according to claim 2 wherein Y is an XR$^a$ group.

4. A compound according to claim 3 wherein L is a —C(R)=C(R$^1$)(R$^2$) group in which R$^1$ and R$^2$, together with the C atom to which they are attached are linked to form a cycloalkyl group.

5. A compound according to claim 1 wherein Z is a group (A) or (B), in which R$^3$, R$^6$ and R$^7$ is each a hydrogen atom, R$^4$ is an aryl group and R$^5$ is a heteroaryl group.

6. A compound according to claim 5 wherein R$^4$ is an optionally substituted phenyl group and R$^5$ is an optionally substituted pyridyl group.

7. A compound which is selected from the group consisting of:

4-{2-[4-Methoxy-3-(phenylpentyloxy)phenyl]-2-phenylethyl}pyridine;

4-[2-(4-Methoxy-3-(3-thienyloxy)phenyl)-2-phenylethyl]pyridine;

4-{2-[3-(4-Biphenyloxy)-4-methoxyphenyl]-2-phenylethyl}pyridine;

4-[2-(3-((2RS)-exo-Bicyclo[2.2.1]hept-2-yloxy)-4-methoxyphenyl)-2-phenylethyl]pyridine;

3-(3-Cyclopentylidenyl-4-methoxyphenyl)pyridine;

the resolved enantiomers; and the salts, solvates, hydrates, prodrugs and N-oxides thereof.

8. A pharmaceutical composition which comprises a compound of formula (1)

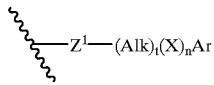

(1)

wherein

=W— is (1) =C(Y)— or (2) =N—;

L is (1) —C(R)=C(R$^1$)(R$^2$) or —(CHR)$_n$CH(R$^1$)(R$^2$), (2) —(X$^a$)$_n$Alk'Ar' or —Alk'X$^a$Ar' or (3) X$^a$R';

Z is a group (A), (B), (C) or (D):

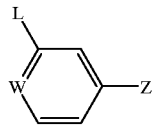

(A)

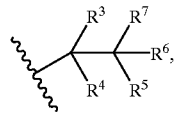

(B)

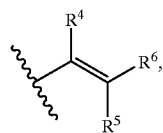

(C)

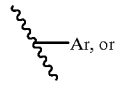

-continued (D)

$$\text{—Z}^1\text{—(Alk)}_t(X)_n\text{Ar}$$

n is zero or the integer 1;

t is zero or an integer 1, 2 or 3;

Y is halogen or an alkyl or —XR$^a$ group;

each of X and X$^a$ is independently —O—, —S(O)$_m$—, or —N(R$^b$)—;

Z$^1$ is —NR$^{12}$C(O)—, —C(O)NR$^{12}$—, —NR$^{12}$C(S)—, —C(S)NR$^{12}$—, —C≡C—, —NR$^{12}$SO$_2$— or —SO$_2$NR$^{12}$—;

m is zero or an integer 1 or 2;

each of R$^a$ and R$^b$ is independently hydrogen or an optionally substituted alkyl group;

R' is Ar' or an optionally substituted polycycloalkyl or polycycloalkenyl group optionally containing one or more —O— or —S— atoms or —N(R$^b$)— groups;

Ar is an optionally substituted monocyclic or bicyclic aryl group optionally containing one or more heteroatoms selected from oxygen, sulphur and nitrogen atoms;

Ar' is an optionally substituted heterocycloaliphatic group or an optionally substituted monocyclic or bicyclic aryl group optionally containing one or more heteroatoms selected from oxygen, sulfur and nitrogen atoms;

Alk is an optionally substituted straight or branched alkylene chain optionally interrupted by an atom or group X;

Alk' is an optionally substituted straight or branched alkylene, alkenylene or alkynylene chain optionally interrupted by one or more linker atoms or groups L$^1$;

R is hydrogen, fluorine or a methyl group;

each of R$^1$ and R$^2$, which may be the same or different, is hydrogen, fluorine, —CN, —NO$_2$, or an optionally substituted alkyl, alkenyl, alkynyl, alkoxy, alkylthio, —CO$_2$R$^8$, —CONR$^9$R$^{10}$ or —CSNR$^9$R$^{10}$ group, or R$^1$ and R$^2$, together with the carbon atom to which they are attached, are linked to form an optionally substituted cycloalkyl, cycloalkenyl or heterocycloaliphatic group;

R$^3$ is hydrogen, fluorine, an optionally substituted straight or branched alkyl group, or —OR$^{11}$;

R$^4$ is hydrogen, —CN, —CH$_2$CN or an optionally substituted —CO$_2$R$^8$, —CSNR$^9$R$^{10}$ or —(CH$_2$)$_t$Ar group;

R$^5$ is —(CH$_2$)$_t$Ar;

R$^6$ is hydrogen, fluorine, —CO$_2$R$^8$, —CONR$^9$R$^{10}$, —CSNR$^9$R$^{10}$, or an optionally substituted alkyl group;

R$^7$ is hydrogen, fluorine, an optionally substituted straight or branched alkyl group, or —OR$^c$, where R$^c$ is hydrogen, formyl or an optionally substituted alkyl, alkenyl, alkoxyalkyl, alkanoyl, carboxamido or thiocarboxamido group;

each of R$^8$, R$^9$ and R$^{10}$ is independently hydrogen or an optionally substituted alkyl, aralkyl or aryl group;

R$^{11}$ is hydrogen, formyl or an optionally substituted alkyl, alkenyl, alkoxyalkyl, alkanoyl, carboxamido or thiocarboxamido group;

R$^{12}$ is hydrogen or an optionally substituted alkyl or —(Alk)$_t$Ar group; and the salts, solvates, hydrates, prodrugs and N-oxides thereof;

with the provisos that when L is a group (2) or (3), then Z is a group (A) or (B) in which $R^4$ is —(CH$_2$)$_t$Ar, when W is =N—, L is methyl, Z is a group (A) or (B) and $R^5$ is phenyl, then at least one of $R^3$, $R^4$, $R^6$ and $R^7$ is other than hydrogen within the atoms or groups defined for $R^3$, $R^4$, $R^6$ $R^7$ hereinabove, when W is =N—, L is methyl, Z is a group (D), $Z^1$ is —C(O)NH— and Ar is phenyl, then n is 1 and/or t is 1, 2 or 3, when W is C(OCH$_3$), L is bicyclo(2.2.1)heptyloxy, Z is a group (B), and $R^4$ and $R^6$ are hydrogen, then $R^5$ is other than 4-(methoxycarbonyl)phenyl within the groups defined for $R^5$ hereinabove, when W is C(OCH$_3$), L is [exo-8,9,10-trinorbornyl-2-oxy] tricycloalkyloxy or benzyloxy, Z is a group D, $Z^1$ is —C(O)NH— and Ar is 3,5-dichloropyrid-4-yl, 2,6-dichlorophenyl or unsubstituted phenyl, then n is 1 and/or t is 1, 2 or 3, and when W is C(OCH$_3$) and L is benzyloxy, then Z is other than a group (C) in which Ar is an optionally substituted nitrogen-containing monocyclic or bicyclic heterocycle within the groups defined for Ar hereinabove;

together with one or more pharmaceutically acceptable carriers, excipients or diluents.

9. A compound of formula (2)

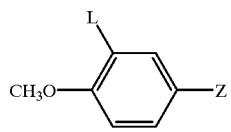

(2)

wherein

L is (1) —C(R)=C($R^1$)($R^2$) or —CH$_2$CH($R^1$)($R^2$), (2) —OAlkAr', or (3) —OR';

Z is a group (A), (B), (C) or (D):

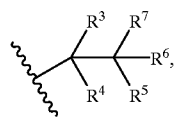

(A)

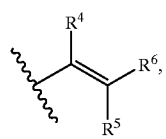

(B)

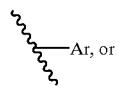

(C)

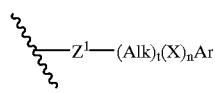

(D)

n is zero or the integer 1;
t is zero or an integer 1, 2 or 3;
X is —O—, —S(O)$_m$—, or —N($R^b$)—;
$Z^1$ is —NR$^{12}$C(O)—, —C(O)NR$^{12}$—, —NR$^{12}$C(S)—, —C(S)NR$^{12}$—, —C≡C—, —NR$^{12}$SO$_2$— or —SO$_2$NR$^{12}$—;
m is zero or an integer 1 or 2;

$R^b$ is hydrogen or an optionally substituted alkyl group;

R' is Ar' or an optionally substituted polycycloalkyl or polycycloalkenyl group;

Ar is an optionally substituted monocyclic or bicyclic aryl group optionally containing one or more heteroatoms selected from oxygen, sulphur and nitrogen atoms;

Ar' is a monocyclic or bicyclic aryl or heteroaryl group;
Alk is a $C_{1-6}$alkylene chain;
R is hydrogen, fluorine or a methyl group;
$R^1$ and $R^2$ are linked together with the carbon atom to which they are attached to form a cycloalkyl group;
$R^3$ is hydrogen, fluorine, an optionally substituted straight or branched alkyl group, or —OR$^{11}$;
$R^4$ is hydrogen, —CN, —CH$_2$CN or an optionally substituted —CO$_2$R$^8$, —CSNR$^9$R$^{10}$ or —(CH$_2$)$_t$Ar group;
$R^5$ is —(CH$_2$)$_t$Ar;
$R^6$ is hydrogen, fluorine, —CO$_2$R$^8$, —CONR$^9$R$^{10}$, —CSNR$^9$R$^{10}$, or an optionally substituted alkyl group;
$R^7$ is hydrogen, fluorine, an optionally substituted straight or branched alkyl group, or —OR$^c$, where $R^c$ is hydrogen, formyl or an optionally substituted alkyl, alkenyl, alkoxyalkyl, alkanoyl, carboxamido or thiocarboxamido group;
each of $R^8$, $R^9$ and $R^{10}$ is independently hydrogen or an optionally substituted alkyl, aralkyl or aryl group;
$R^{11}$ is hydrogen, formyl or an optionally substituted alkyl, alkenyl, alkoxyalkyl, alkanoyl, carboxamido or thiocarboxamido group;
$R^{12}$ is hydrogen or an optionally substituted alkyl or —(Alk)$_t$Ar group; and the salts, solvates, hydrates, prodrugs and N-oxides thereof;

with the provisos that when L is a group (2) or (3), then Z is a group (A) or (B) in which $R^4$ is —(CH$_2$)$_t$Ar, when L is bicyclo(2.2.1)heptyloxy, Z is a group (B), and $R^4$ and $R^6$ are hydrogen, then $R^5$ is other than 4-(methoxycarbonyl)phenyl within the groups defined for $R^5$ hereinabove, when L is [exo-8,9,10-trinorbornyl-2-oxy] tricycloalkyloxy or benzyloxy, Z is a group D, $Z^1$ is —C(O)NH— and Ar is 3,5-dichloropyrid-4-yl, 2,6-dichlorophenyl or unsubstituted phenyl, then n is 1 and/or t is 1, 2 or 3, and when W is C(OCH$_3$) and L is benzyloxy, then Z is other than a group (C) in which Ar is an optionally substituted nitrogen-containing mocyclic or bicyclic heterocycle within the groups defined for Ar hereinabove.

10. A compound according to claim 9 wherein L is —OAlk'Ar'.

11. A compound according to claim 10 wherein L is selected from benzyloxy, thienyloxy and phenylpentyloxy.

12. A compound according to claim 9 wherein L is OR'.

13. A compound according to claim 12 wherein R' is optionally substituted bicyclo(2.2.1)heptyl or bicyclo(2.2.1)heptenyl.

14. A compound according to claim 12 wherein Z is group (A).

15. A compound according to claim 14 wherein $R^3$, $R^6$ and $R^7$ are hydrogen.

16. A compound according to claim 15 wherein R' is bicyclo(2.2.1)heptyl.

17. A compound according to claim 15 wherein $R^4$ is optionally substituted phenyl or optionally substituted pyridyl, and $R^5$ is optionally substituted pyridyl.

* * * * *